United States Patent
Pedersen et al.

(10) Patent No.: US 8,968,770 B2
(45) Date of Patent: Mar. 3, 2015

(54) MULTI-PART KIT COMPRISING A CHEWING GUM AND FURTHER A FLAVOR CONTAINING FORMULATION

(75) Inventors: Kurt Møller Pedersen, Give (DK); Jette Bæk Andersen, Vejle (DK)

(73) Assignee: Fertin Pharma A/S (DK)

( * ) Notice: Subject to any disclaimer, the term of this patent is extended or adjusted under 35 U.S.C. 154(b) by 326 days.

(21) Appl. No.: 13/164,637

(22) Filed: Jun. 20, 2011

(65) Prior Publication Data

US 2011/0250150 A1 Oct. 13, 2011

Related U.S. Application Data

(63) Continuation of application No. PCT/DK2008/000442, filed on Dec. 19, 2008.

(51) Int. Cl.
| | | |
|---|---|---|
| A61K 9/68 | (2006.01) | |
| A01N 43/40 | (2006.01) | |
| A61K 31/44 | (2006.01) | |
| A23G 4/06 | (2006.01) | |
| A23G 4/18 | (2006.01) | |
| A23G 4/20 | (2006.01) | |

(52) U.S. Cl.
CPC .............. A61K 9/0058 (2013.01); A23G 4/06 (2013.01); A23G 4/18 (2013.01); A23G 4/184 (2013.01); A23G 4/20 (2013.01)
USPC .............................. 424/440; 424/48; 514/343

(58) Field of Classification Search
USPC ........................... 426/5; 514/343; 424/48, 440
See application file for complete search history.

(56) References Cited

U.S. PATENT DOCUMENTS

| | | | |
|---|---|---|---|
| 1,193,423 | A | 8/1916 | Pryor |
| 5,227,154 | A | 7/1993 | Reynolds |
| 5,300,305 | A | 4/1994 | Stapler et al. |
| 5,378,131 | A | 1/1995 | Greenberg |
| 5,679,397 | A | 10/1997 | Kuroda et al. |
| 5,866,179 | A | 2/1999 | Testa |
| 6,235,318 | B1 | 5/2001 | Lombardy, Jr. et al. |
| 6,350,480 | B1 * | 2/2002 | Urnezis et al. ................. 426/5 |
| 6,436,899 | B2 | 8/2002 | Portman |
| 6,468,962 | B1 | 10/2002 | Portman |
| 6,471,945 | B2 | 10/2002 | Luo et al. |
| 6,479,071 | B2 | 11/2002 | Holme et al. |
| 6,485,739 | B2 | 11/2002 | Luo et al. |

(Continued)

FOREIGN PATENT DOCUMENTS

| | | |
|---|---|---|
| EP | 1693085 A1 | 8/2006 |
| WO | 02102357 A1 | 12/2002 |

(Continued)

OTHER PUBLICATIONS

International Search Report; PCT/DK2008/000442; Sep. 14, 2009; 4 pages.

*Primary Examiner* — Benjamin Packard
(74) *Attorney, Agent, or Firm* — St. Onge Steward Johnston & Reens LLC

(57) ABSTRACT

A multi-part kit for administering at least one active pharmaceutical ingredient including at least one piece of chewing gum including the active pharmaceutical ingredient, the piece of chewing gum comprising gum base; and at least one further flavor-containing formulation; wherein the gum base content of the at least one further flavor-containing formulation is less than 70% by weight of the gum base content of said piece of chewing gum.

24 Claims, 3 Drawing Sheets

(56) References Cited

U.S. PATENT DOCUMENTS

| | | |
|---|---|---|
| 6,558,690 B2 | 5/2003 | Portman |
| 6,685,916 B1 | 2/2004 | Holme et al. |
| 6,696,044 B2 | 2/2004 | Luo et al. |
| 6,716,815 B2 | 4/2004 | Portman |
| 6,733,818 B2 | 5/2004 | Luo et al. |
| 6,838,431 B2 | 1/2005 | Portman |
| 6,846,500 B1 | 1/2005 | Luo et al. |
| 8,024,911 B2 * | 9/2011 | Hultberg et al. ............... 53/411 |
| 2001/0021694 A1 | 9/2001 | Portman |
| 2001/0043907 A1 | 11/2001 | Luo et al. |
| 2002/0071858 A1 | 6/2002 | Luo et al. |
| 2002/0098157 A1 | 7/2002 | Holme et al. |
| 2002/0110580 A1 | 8/2002 | Portman |
| 2002/0119915 A1 | 8/2002 | Portman |
| 2002/0159955 A1 | 10/2002 | Luo et al. |
| 2003/0008810 A1 | 1/2003 | Portman |
| 2003/0099741 A1 | 5/2003 | Gubler |
| 2003/0157213 A1 | 8/2003 | Jenkins |
| 2003/0203993 A1 | 10/2003 | Katsumura et al. |
| 2003/0206993 A1 | 11/2003 | Gubler |
| 2003/0215417 A1 | 11/2003 | Uchiyama et al. |
| 2004/0037788 A1 | 2/2004 | Barreca |
| 2004/0081713 A1 | 4/2004 | Maxwell et al. |
| 2004/0136928 A1 | 7/2004 | Holme et al. |
| 2005/0008732 A1 | 1/2005 | Gebreselassie et al. |
| 2005/0025721 A1 | 2/2005 | Holme et al. |
| 2006/0051455 A1 * | 3/2006 | Andersen et al. ............... 426/3 |
| 2006/0263474 A1 | 11/2006 | Luo |

FOREIGN PATENT DOCUMENTS

| | | |
|---|---|---|
| WO | 2004098305 A1 | 11/2004 |
| WO | 2004098306 A1 | 11/2004 |
| WO | 2006000232 A1 | 1/2006 |
| WO | 2006079342 A1 | 8/2006 |

* cited by examiner

MULTI-PART KIT COMPRISING A CHEWING GUM AND FURTHER A FLAVOR CONTAINING FORMULATION

CROSS-REFERENCE TO RELATED APPLICATIONS

The present application is a continuation of pending International patent application PCT/DK2008/000442 filed on Dec. 19, 2008 which designates the United States and the content of which is incorporated herein by reference.

FIELD OF THE INVENTION

The present invention relates to a multi-part kit comprising chewing gum with active pharmaceutical ingredients.

BACKGROUND OF THE INVENTION

A large number of active pharmaceutical ingredients may be administered by the use of a chewing gum. An example of this is known from e.g. WO 02/102357 disclosing a coated nicotine-containing chewing gum.

The use of chewing gum to administrate nicotine has been known for several years, in which the nicotine may be mixed with the gum base and/or added as part of the coating.

The addition of nicotine as part of the coating often favors a fast release of the nicotine; however with too fast release, substantial amounts of the nicotine may be lost because it reaches the stomach and is digested without providing the desired relief from cravings. Hereby it may happen that only a minor part of the fast released nicotine is being absorbed by the mucous membrane, where it becomes effective.

The mixing of nicotine with the gum base may be an alternative. Nicotine release from the gum base may be comparatively slow and the nicotine release may be adjusted to cover a prolonged period of time. However the release of nicotine from the gum base may in this case end up being too slow whereby a significant amount of the nicotine is trapped in the gum base and not released to relief nicotine cravings.

A challenge related to the use of active pharmaceutical ingredients in chewing gum is that the active pharmaceutical ingredients should be administered as effectively as possible to the user. In the case of nicotine as the active pharmaceutical ingredient this includes both the amount of nicotine absorbed through the mucous membrane and the amount of nicotine in the chewing gum actually released and utilized to relief the cravings of the user, thereby providing an effective alternative to the smoking of a cigarette.

It is an object of the present invention to provide an improved and effective administration of active pharmaceutical ingredients such as nicotine to users of medicated chewing gum.

SUMMARY OF THE INVENTION

The invention relates to a multi-part kit for administering at least one active pharmaceutical ingredient comprising:
- at least one piece of chewing gum comprising said active pharmaceutical ingredient, said piece of chewing gum comprising gum base; and
- at least one further flavor-containing formulation;
- wherein the gum base content of said at least one further flavor-containing formulation is less than 70% by weight of the gum base content of said piece of chewing gum.

With the multi-part kit according to the present invention the active pharmaceutical ingredient (API) is more effectively administered to the user in that the piece of API-chewing gum from a multi-part kit according to the present invention may typically be kept in the mouth for a prolonged period as compared to prior art in that a pleasant taste is maintained throughout the chewing process. This is made possible in that a good taste may be supplemented and varied throughout the chewing process by the co-administering of the flavor-containing formulation of the multi-part kit. In this context formulation should be broadly understood, as defined later.

This is highly interesting because due to an often seen faster release of flavor than of API, the taste of the chewing gum tends to worsen over time and therefore often it is not appealing for the user to keep the chewing gum in the mouth for longer time than time periods such as 10 or maybe 15 minutes. For a number of APIs such as nicotine, it is highly preferred that the user keeps the chewing gum in the mouth for minimum 30 minutes in order to absorb a satisfying part of the API of the chewing gum.

With the present invention this utilization of API has been improved. The API is very often the most expensive part of a chewing gum comprising such API. As such it is desired that a larger part of the API is utilized. This is made possible according to the present invention by enabling the user to supplement the chewing gum comprising API with flavor-containing formulations when the taste-level of the chewing gum drops. Hereby the average time the chewing gum is kept in the mouth may be prolonged.

If supplementing the taste with further pieces of chewing gum of approximately the same composition, some problems may occur. Using further identical pieces comprising the same API may result in overdosing of the API and furthermore an inefficient use of the API as the resulting chewing gum will be dropped at least before the API of the last supplementing piece has been sufficiently administered.

As such it may instead be advantageous to supplement with further formulations without the API. However, this does not solve all problems. First of all a number of further pieces would result in a markedly higher remainder in the mouth, which would soon make the chewing unpleasant to the user. Secondly it is very important that the API is released and absorbed in the oral cavity of the user; with such markedly higher remainder in the mouth it is very likely that the API may be bound to this remainder instead of being absorbed.

With the present invention, the content of gum base in the flavor-containing formulation is kept lower than the content in the chewing gum, hereby providing a possible solution to the above-mentioned problems. Hereby the remainder in the mouth may be kept relatively low even after supplementing with a number of flavor-containing formulation and thereby uphold the pleasure by chewing the chewing gum for a prolonged time. Moreover the API may have a lower tendency towards being bound to a corresponding lower amount of remainder. Moreover the addition of flavor by the flavor-containing formulation gives a more pleasant taste sensation to the user when it is added to a lower amount of remainder, in that the relative amount of flavor as compared to the remainder is larger.

It is noted that the problem of too high amount of resulting gum base through several additional formulations cannot be solved by markedly lowering the amount of gum base in the starting chewing gum; in this case the API may risk to be too fast released from the chewing gum in the starting phase. Hence, with the typical gum bases known presently, the starting amount of gum base should not be too low either. Moreover with a small amount of gum base, if the volume in the mouth decreases too fast during chewing, the user may get a feeling of too little substance for chewing.

Moreover with the present invention the individual users of the chewing gum may find the chewing of medicated chewing gum much more pleasant than in prior art. When taste is beginning to decrease, the chewing gum may be supplemented with further flavor from a flavor-containing formulation, thereby sustaining a pleasurable chewing experience.

A further advantage of the present invention is that with an improved taste-level, the users will chew each individual chewing gum for a longer period, possibly resulting in a decreased number of chewed chewing gum pieces containing the API each day. In this way the risk of an unacceptable high dosing of the API is lessened. When a larger amount of the API from each piece of chewing gum is absorbed by the user, a better idea is present of how large an amount of API the user has absorbed per day. This is important, due to the fact that for some APIs, such as nicotine, it may be unpleasant and even dangerous to receive too large an amount of the API. It is noted that the release rate of API is highest in the beginning phase; hence it is problematic to add with a new nicotine-containing piece of chewing gum each time instead of chewing for at longer time. In this way the user may as well save money in that flavor-containing formulations most often will be cheaper than a chewing gum comprising an API, as API may be the most expensive part of the chewing gums.

In the case where the API is nicotine, the purpose of chewing the chewing gum is most often to quit smoking. In this case it may be advantageous with the bad taste of nicotine during chewing, hopefully encouraging users to reduce the number of nicotine chewing gums per day and thereby lessen the daily uptake of nicotine and ultimately completely stop from nicotine craving. With the present invention, it may also be attractive to use a piece of chewing gum as alternative to a cigarette and the possibility of sharing from the multi-part kit is present, in that flavor-containing pellets without API may be digested by anyone as sweets.

When using the chewing gum as an alternative to a cigarette, this can be as supplement to normal smoking when e.g. there is no time for picking up new cigarettes in the shop, when on a plane or the like where smoking is prohibited, when working in a place where smoking is only outdoor, when stopping smoking only temporarily etc.

In an embodiment of the invention, said at least one further flavor-containing formulation comprises gum base.

In an embodiment of the invention, said at least one further flavor-containing formulation is substantially free of gum base.

In an embodiment of the invention, the gum base content of said at least one further flavor-containing formulation is less than 60% by weight, preferably less than 40% by weight of the gum base content of said at least one piece of chewing gum.

In further embodiments of the invention the gum base content of said at least one further flavor-containing formulation is less than 30% by weight or less than 20% by weight of the gum base content of said at least one piece of chewing gum.

In an embodiment of the invention, the gum base content of said at least one further flavor-containing formulation is more than 1% by weight, preferably more than 4% by weight, more preferably more than 8% by weight of the gum base content of said at least one piece of chewing gum.

In an embodiment of the invention, the amount of gum base of said at least one piece of chewing gum is more than 50 mg, preferably more than 100 mg, more preferably more than 200 mg, and most preferably more than 300 mg.

For most APIs it is preferred that the release of the API happens over time, hence preferably the chewing gum comprises a minimum amount of gum base to aid in holding back the API.

In an embodiment of the invention, the amount of gum base of said at least one piece of chewing gum is less than 2000 mg, preferably less than 1000 mg, most preferably less than 800 mg.

In order to avoid a too large remainder in the mouth of the user, preferably the gum base content of the starting piece of chewing gum should not be too large.

In an embodiment of the invention, the amount of gum base of said at least one further flavor-containing formulation is less than 600 mg and preferably less than 300 mg.

In order to be able to supplement the piece of chewing gum comprising the API with additional flavor from the flavor-containing formulation without a too large remainder in the mouth of the user as the result, preferably the gum base content of said flavor-containing formulation should not be too large.

In further embodiments the amount of gum base of said at least one further flavor-containing formulation is less than 200 mg or less than 100 mg In an embodiment of the invention, the weight of said at least one piece of chewing gum is below 8000 mg, preferably below 2000 mg.

In an embodiment of the invention, the weight of said at least one piece of chewing gum is above 100 mg, preferably above 200 mg.

In some embodiments of the invention, the weight of each piece of chewing gum is more than 400 mg, or more than 600 mg.

In an embodiment of the invention, the weight of each of said at least one further flavor-containing formulation is less than 3000 mg, preferably less than 1000 mg, more preferably less than 600 mg.

In some embodiments of the invention, the weight of each of said at least one further flavor-containing formulation is less than 800 mg or less than 300 mg.

In an embodiment of the invention, said at least one piece of chewing gum comprises flavor.

According to various embodiments of the present invention the user may lessen the problem of bad taste from an API such as nicotine in that flavor may be used as taste masking in chewing gum comprising active ingredients, which by themselves have undesired taste or which alter the taste of the formulation, and instead maintain a satisfying taste of the chewing gum during the chewing process, including possible supplementing with flavor-containing formulations.

According to preferred embodiments of the invention, the chewing gum piece(s) comprises one or more flavors. This may ensure a pleasure directly upon chewing the chewing gum even though it comprises an API.

In an embodiment of the invention, said at least one piece of chewing gum is substantially free of flavor.

According to other embodiments of the invention, the chewing gum piece(s) holds a low amount of flavor and sweetener, maybe even substantially free of flavor, in order to make these unattractive to children, in case small children should get hold of the chewing gum and put it in the mouth. Also, because some API may be altered or destroyed by certain flavoring agents, it may be beneficial for API stability to avoid flavor in the API-chewing gum.

In an embodiment of the invention, at least one of said at least one further flavor-containing formulation comprises a flavor different from any flavor in said at least one piece of chewing gum.

According to embodiments of the invention, the flavor in the flavor-containing formulation gives a variation in the taste, which is present from chewing said chewing gum.

By stating that two flavors are different may be meant that the perceptual experience to the user is different for the two flavors. Hereby is achieved that the user is given great opportunities of varying the taste during the chewing process of the chewing gum by supplementing with the flavor-containing formulations.

In an embodiment of the invention, at least one of said at least one further flavor-containing formulation comprises a flavor being the same as a flavor in said at least one piece of chewing gum.

In an embodiment of the invention, said at least one further flavor-containing formulation comprises at least one, preferably at least two formulations with different flavors.

According to embodiments of the invention, the multi-part kit comprises flavor-containing formulations with varying flavor to give variation in the taste, i.e. different flavors are contained in different pieces of the flavor-containing formulations. Hereby it is made possible for the user to vary the taste accordingly when supplementing with further flavor-containing formulations during the chewing process instead of maintaining the same taste for 30 min. Hereby the chewing process may be made more pleasant.

According to further embodiments of the invention, said at least one further flavor-containing formulation comprises at least three or at least four formulations with different flavors.

In an embodiment of the invention, said multi-part kit in total comprises at least two different flavors of said chewing gum and said further flavor-containing formulation.

In order to vary the possibilities for the user it may be advantageous to vary the flavor; hence various flavors may be present in the multi-part kit. In further embodiments of the invention, three, four, five, six or more different flavors may be used in the same multi-part kit as part of the chewing gum, the flavor-containing formulations or both.

In an embodiment of the invention, said at least one further flavor-containing formulation comprises flavor in an amount of above 0.1%, preferably above 1% by weight of said flavor-containing formulation.

In further embodiments of the invention, said at least one further flavor-containing formulation may comprise flavor in an amount of above 0.5%, 2%, 3% or 4% by weight of said flavor-containing formulation.

In various embodiments of the invention, said at least one further flavor-containing formulation is selected from the group consisting of a pellet, a bead, a capsule, a stick, a powder, a liquid, a gum pellet, a tablet, or any combination thereof.

In an embodiment of the invention, said at least one further flavor-containing formulation forms a further piece.

In an embodiment of the invention, said at least one further flavor-containing formulation is a pellet.

Both piece and pellet should in this context be broadly understood to mean a pastille-like supplementary item, not restricted to a certain shape, content nor size, but may resemble a small chewing gum, pastille, boiled sweets or the like.

A specific type of the pellet is the gum pellet, which in content may resemble a chewing gum comprising gum base.

In various embodiments of the invention said gum base comprises elastomer and resin. Suitable elastomer and resin to be used according to embodiments of the present invention may be seen from the detailed description.

In various embodiments of the invention said resin comprises natural resins constituting an amount in the range of 0.1 to 40%, preferably 1 to 20% by weight of said at least one piece of chewing gum and synthetic resins constituting an amount in the range of 0.1 to 40%, preferably 1 to 20% by weight of said at least one piece of chewing gum. Moreover said gum base typically comprises elastomer constituting an amount in the range of 0.1 to 20%, preferably 1 to 15% by weight of said at least one piece of chewing gum.

In an embodiment of the invention, said chewing gum comprises high intensity sweeteners in an amount of less than 2%, preferably less than 1%, and more preferably less than 0.5% by weight of the said chewing gum.

In an embodiment of the invention, said chewing gum comprises bulk sweetener in an amount of at least 1%, preferably at least 10%, and more preferably at least 20% by weight of the chewing gum.

In an embodiment of the invention, said chewing gum comprises low calorie bulking agents in an amount of at least 1%, preferably at least 2% by weight of the chewing gum.

Various examples of low calorie bulking agents may be polydextrose, cellulose, starch, bran, glucans, hydrocolloids, and the like.

In an embodiment of the invention, said at least one further flavor-containing formulation comprises bulk-sweetener.

In an embodiment of the invention, said at least one further flavor-containing formulation comprises high-intensity sweetener.

In preferred embodiments of the present invention, the flavor-containing formulations also comprise bulk-sweetener and/or high-intensity sweetener, which may improve the taste of the chewing gum as well. Indeed sweeteners may improve the sensation from flavor.

In an embodiment of the invention, said at least one further flavor-containing formulation comprises flavor selected from the group consisting of cinnamon, wintergreen, spearmint, orange, tutti, peppermint, menthol and lemon.

In various embodiments of the invention, said flavor may be selected from the group consisting of lemon, blackcurrant, coconut, coffee, chocolate, vanilla, grape fruit, cranberry, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, mint, fruit essence such as from apple, pear, peach, strawberry, apricot, raspberry, cherry, pineapple, and plum essence, essential oils including peppermint, spearmint, menthol, eucalyptus, clove oil, bay oil, anise, thyme, cedar leaf oil, nutmeg, cola, tea tree oil, green tea, cooling and heating agents, oils of the fruits mentioned above and combinations thereof.

The list of flavors mentioned here should not be considered as exhaustive but merely as examples of various flavors which may be used according to various embodiments of the present invention.

In an embodiment of the invention, said active pharmaceutical ingredient is lipophilic.

For lipophilic API the optimal chewing time to release a sufficient amount of API may often be above 20 minutes, typically about 30 minutes.

In an embodiment of the invention, said active pharmaceutical ingredient is hydrophilic.

For hydrophilic API the chewing time to release a sufficient amount of API may be quite low, maybe about 5-10 minutes; however a number of further broader time intervals may be advantageous as well depending on the API in question.

In an embodiment of the invention, said active pharmaceutical ingredient is a tobacco alkaloid, preferably nicotine, wherein said nicotine is in a form selected from nicotine salts, nicotine free base, encapsulated nicotine, nicotine bound in a complex, or any combination thereof.

According to various embodiments of the present invention, said complex comprises an ion exchange resin or an adsorbent. Said ion exchange resin may be a weakly acidic cation exchange resin and said adsorbent may be selected from the group consisting of finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, or any combination thereof.

In an embodiment of the invention, said at least one active pharmaceutical ingredient is selected from the group consisting of cetirizine, levo cetirizine, metformin, metformin HCL, phenylephrine, GLP-1, exenatide, MC-4 receptor antagonist, PPY(3-36), deca-peptide, KSL-W (acetate), fluor, and chlorhexidine.

In an embodiment of the invention, said at least one chewing gum piece comprises an additional active ingredient.

In an embodiment of the invention, said at least one further flavor-containing formulation comprises an active ingredient.

According to an embodiment of the present invention, more than one API may be added to the components of the multi-part kit. If for instance two API are synergetic, but not directly compatible in one single API-chewing gum, the two synergistic API may be administered by use of embodiments of the present invention In an embodiment of the invention, said active pharmaceutical ingredient is an absorption enhancer such as a pH-controlling components.

An example is that the piece of chewing gum comprises nicotine and a suitable buffer for maintaining a satisfying pH-value in the buccal cavity is added through the flavor-containing formulation. Another example is addition of a mild anesthetic to dampen receptors, which may otherwise react to the presence of API in the oral cavity. Obviously a number of further embodiments with additional API are within the scope of the present invention.

In an embodiment of the invention, said pH-controlling components are selected from the group of sodium carbonate, sodium hydrogen carbonate, potassium carbonate, potassium hydrogen carbonate, dipotassium phosphate, potassium citrate, or any combination thereof.

In an embodiment of the invention, said pH-controlling components are implying a pH value in the range of 7.4 to 10 in the buccal cavity of a user of said chewing gum.

In an embodiment of the invention, said at least one further flavor-containing formulation is substantially free of active pharmaceutical ingredients.

In an embodiment of the invention, said flavor-containing formulation comprises a coloring agent.

According to advantageous embodiments of the invention, the individual flavor-containing formulations may be colored to indicate to the user that various tastes are present. For instance a pellet with a liquorice taste may be black; one with strawberry taste may be red, etc.

According to a further embodiment of the invention, said piece of chewing gum may comprise a coloring agent as well. The color of the chewing gum and the pellets may be paired if the chewing gum flavor is present in one or more of the pellets, in order for the user to supplement easily with the same taste.

The use of a neutral colored, such as white, chewing gum comprising API and possibly more attractive richly colored pellets may be used as a further child-proof mechanism.

In an embodiment of the invention, different colors of said flavor-containing formulation are used to indicate different tastes of said flavor-containing formulation.

According to a further embodiment of the invention, said at least one further flavor-containing formulation is center-filled.

For example the flavor-containing formulation may be a gelatine-capsule comprising a liquid flavor alone or in combination with e.g. one or more sweeteners.

Another possibility is that the flavor-containing formulation may be a gum pellet with a center-filling of some flavor combination surrounded by a chewing gum formulation.

In an embodiment of the invention, the ratio between number of flavor-containing formulations and number of pieces of chewing gum of said multi-part kit is above 2, preferably above 3.

In further embodiments of the invention, the ratio between number of flavor-containing formulations and number of pieces of chewing gum of said multi-part kit is above 4 or above 6.

In further embodiments of the invention, said multi-part kit comprises at least two compartments, one of said compartments comprises said at least one piece of chewing gum and another of said compartments comprises said at least one further flavor-containing formulations.

In further embodiments of the invention, said multi-part kit may comprise three, four, five, or more compartments, wherein typically one or two of the compartments may comprise the chewing gum pieces and the remaining compartments may comprise the further flavor-containing formulations.

According to further embodiments of the invention, said flavor-containing formulation is compressed in one or more modules, such as layers.

According to a further embodiment of the invention, said at least one piece of chewing gum is center-filled.

In an embodiment of the invention, said chewing gum is a compressed chewing gum.

According to further embodiments of the invention, said compressed chewing gum comprises at least one module, preferably at least two modules. According to embodiments of the invention, said modules are layers.

According to further embodiments of the invention, said gum base comprises at least one biodegradable polymer. If biodegradable polymers are used in the gum base of the API-chewing gum and/or a possible gum base of the flavor-containing formulation, advantageous embodiments of the present invention have been obtained relating to environmental concerns.

According to further embodiments of the invention, said chewing gum and/or said flavor-containing formulation comprise a coating. According to embodiments of the invention, the coating of the chewing gum and/or the flavor-containing formulation may be selected from a hard coating, a soft coating, a film coating or combinations thereof.

In an embodiment of the invention, said multi-part kit comprises individually sealed compartments, preferably said multi-part kit is a blister-package.

A so-called blister package where a number of chewing gum pieces are kept in individually sealed compartments may conveniently be used for embodiments of the present invention when isolation of individual pieces of API-chewing gum and/or individual portions of flavor-containing formulation is desired. An advantageous example is a blister-package with one piece of nicotine-containing chewing gum in combination with 12 flavor-containing pellets.

In an embodiment of the invention, said multi-part kit is a plastic box.

According to an embodiment of the present invention, said plastic box may comprise a flip-action living hinge lid to facilitate easy access to the chewing gum and/or the flavor-containing formulations. The plastic box may e.g. comprise a jar, a tub or any other suitable package system.

According to further embodiments of the invention, the multi-part kit may be refilled with chewing gum and/or flavor-containing formulations. Such may be sold in economy packaging e.g. an aluminum foil bag or another suitable container. By prolonging the life time of the multi-part kit in this way, it may be more attractive to manufacture the multi-part kit in quality materials, with a smart design, or the like.

In further embodiments of the invention, the multi-part kit may be a bag, a cardboard box, or other suitable package known by the skilled person.

In an embodiment of the invention, said multi-part kit comprises
- at least one piece of chewing gum comprising gum base and nicotine; and
- one or more pieces of flavor-containing pellets comprising gum base,
- wherein the gum base content of said pieces of flavor-containing pellets is less than 70% by weight of the gum base content of said piece of chewing gum.

Moreover the invention relates to an assortment of at least two multi-part kits;
- each of said at least two multi-part kits comprises at least one piece of chewing gum comprising at least one active pharmaceutical ingredient, and
- each of said at least two multi-part kits further comprises at least one further flavor-containing formulation;
- said at least one piece of chewing gum comprises gum base;
- said at least one active pharmaceutical ingredient of the individual pieces of chewing gum is the same for each of the at least two multi-part kits; and
- flavor-containing formulation of a first multi-part kit comprises at least one flavor different from flavors of flavor-containing formulation of a second multi-part kit.

From the manufacturer's point of view it is highly favorable to manufacture an assortment, in which one approval from the authorities related to the piece of chewing gum comprising the API enables the manufacturer to market and sell multi-part kits comprising these pieces of chewing gum with a number of combinations of flavor-containing formulations, making it easier to apply for an approval from the authorities again.

Moreover, when providing an assortment of two or more multi-part kits several advantages may be obtained. Each multi-part kit of the assortment may correspond to a certain dosage, e.g. a day's use, thereby lessening the burden on the user to keep track of the consumption of API-chewing gum. Furthermore, the available flavors of the flavor-containing compositions may vary for each multi-part kit of the assortment, thereby providing pleasant and surprising taste-variations to the user, making the supplementing of flavor while chewing the API-chewing gum even more attractive.

In an embodiment of the invention, the gum base content of said at least one further flavor-containing formulation is less than 70% by weight of the gum base content of said piece of chewing gum.

Moreover the invention relates to an assortment of at least two multi-part kits, wherein said multi-part kits are multi-part kits according to any of the above-described embodiments.

Moreover the invention relates to a method of administering at least one pharmaceutically active ingredient being part of a multi-part kit comprising the steps of
- administering at least one piece of chewing gum comprising said at least one pharmaceutically active ingredient, and
- administering at least one further flavor-containing formulation after a time interval of chewing said piece of chewing gum to maintain a satisfying taste for a longer period of time while releasing said pharmaceutically active ingredient.

In an embodiment of the invention, the time interval between administering said at least one piece of chewing gum to administering said at least one further flavor-containing formulation is at least 15 seconds, preferably at least 1 minute and most preferably at least 2 minutes.

According to embodiments of the present invention the chewing gum is supplemented with flavor-containing formulation after certain time intervals, which dependent on the individual user may be about 1, 2, 3, 4, 5, 6, or 7 minutes.

In an embodiment of the invention, the time interval between administering said at least one piece of chewing gum to administering said at least one further flavor-containing formulation is at most 20 minutes, preferably at most 12 minutes.

In an embodiment of the invention, said at least one further flavor-containing formulation is supplemented with at least one further flavor-containing formulation after at least about 3 to 9 minutes, and again after at least about 10 to 18 minutes.

In an embodiment of the invention, said at least one further flavor-containing formulation is supplemented with at least one further flavor-containing formulation after at least about 3 to 7 minutes, again after at least about 7 to 12 minutes, again after at least about 12 to 18 minutes, and again after at least about 18 to 28 minutes.

In an embodiment of the invention, said at least one further flavor-containing formulation is supplemented with at least one further flavor-containing formulation after about 5 minutes, again after about 10 minutes, again after about 15 minutes, again after about 20 minutes and again after about 25 minutes.

In an embodiment of the invention, chewing said piece of chewing gum continues for more than 5, preferably more than 10 minutes.

Moreover the invention relates to a use of a multi-part kit according to any of the above-described embodiments to administer at least one pharmaceutically active ingredient.

BRIEF DESCRIPTION OF THE DRAWINGS

The invention will be described with reference to the drawings of which

DETAILED DESCRIPTION OF THE INVENTION

Within the present context, the term active pharmaceutical ingredient (API) covers pharmaceutically active ingredients in general, examples of which are found below.

The term API chewing gum covers chewing gum comprising at least one API.

The term formulation is meant to broadly cover a number of variations such as pellets, beads, sticks or the like. According to some embodiments of the invention, the formulation may be pellets.

The term gum base covers water-insoluble and organic material.

The term multi-part kit covers a kit, wherein multiple parts are together in one kit. In preferred embodiments this is multiple compartments bound together through e.g. a common back or simply through a common structure, which may be box-like or the like.

With the term "end up being too slow" in the background section is meant too slow relative to the normal time a user will keep the chewing gum in the mouth. In other words, in many applications the release over a period may not be too slow as such because it is intended that at least 30 minutes must be applied to release the API. The problem may be that the user may choose to terminate the intended chewing process prematurely e.g. due to a bad taste.

With the present invention as described herein are obtained improvements relating to administering of API in chewing gum both with relation to efficiency of utilization of the API and with relation to taste experiences to the user of the API chewing gum.

In the embodiments described below with reference to the drawings and furthermore in the examples, the flavor-containing formulations are described as and labeled flavor-containing pellets or simply just pellets.

Figure 1:
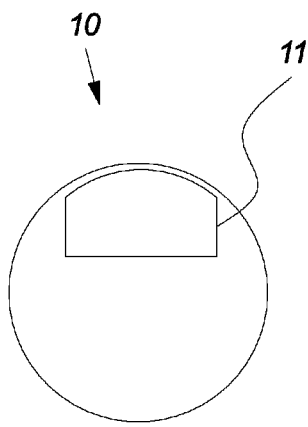
FIG. 1 illustrates a multi-part kit according to a first embodiment of the present invention seen from one side.

A multi-part kit 10 according to a first embodiment of the present invention is shown in FIG. 1, seen from one side. On this side is a lid 11, behind which is a compartment comprising pieces of chewing gum comprising an API may be found.

Figure 2:
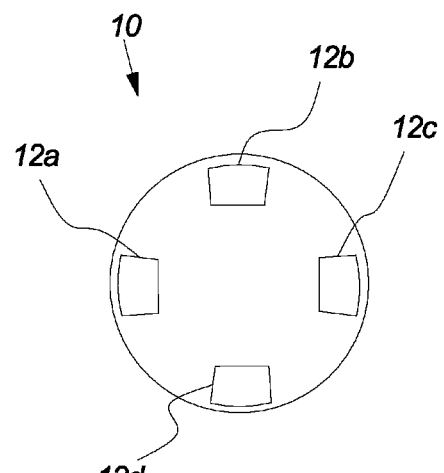
FIG. 2 illustrates the multi-part kit of FIG. 1 seen from another side.

In FIG. 2 is seen the same multi-part kit 10 turned upside-down. In the shown embodiment this side comprises 4 different lids 12a, 12b, 12c, 12d, each of which opens to a compartment comprising pieces of flavor-containing pellets. As an example lid 12a may open to flavor-containing pellets with strawberry flavor, lid 12b to pellets with mint flavor, lid 12c to pellets with orange flavor and lid 12d to pellets with cinnamon flavor.

Obviously the flavor of the pellets behind the individual lids may be varied in numerous ways according to different embodiments of the present invention. Any combination of different flavors may be used and e.g. two different lids may open into pellets with the same flavor, if one flavor is favored and the number of lids is kept the same due to e.g. appearance of the multi-part kit 10.

Moreover the number and position of the lids may be adjusted according to individual desires.

The lids 11, 12a, 12b, 12c, 12d may be any conventional type of lid, which will be known to the skilled person. One possibility would be to make the lids child-proof.

Figure 3:
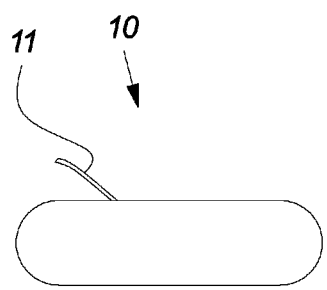
FIG. 3 illustrates the multi-part kit of FIG. 1 seen from yet another side.

In FIG. 3 is seen the same multi-part kit 10 from the side, where the lid 11 is in an opened position.

Figure 4:
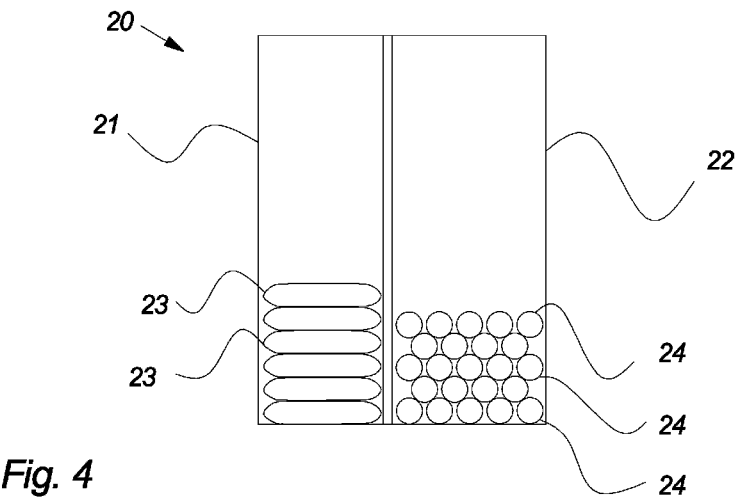
FIG. 4 illustrates a multi-part kit according to a second embodiment of the present invention.

FIG. 4 discloses another embodiment of the present invention. Here the multi-part kit 20 comprises two compartments 21, 22, each of which may be opened individually through lids (not shown). The first compartment 21 comprises pieces 23 of chewing gum comprising API, and the second compartment 22 comprises flavor-containing pellets 24 with a certain flavor, e.g. spearmint.

Figure 5:
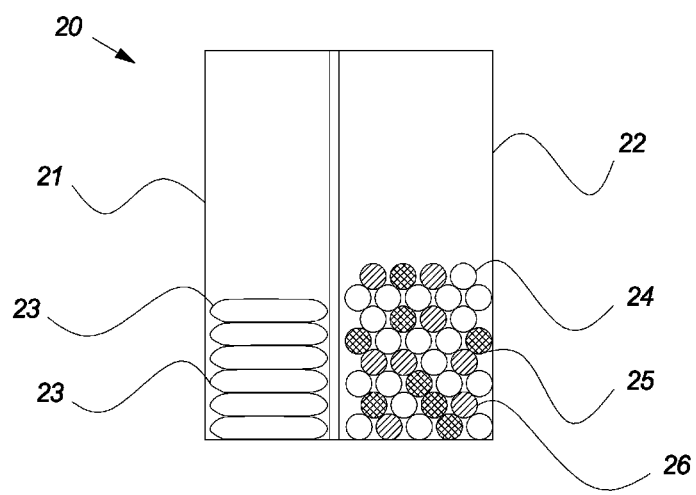
FIG. 5 illustrates a variation of the multi-part kit of FIG. 4, and FIGS. 6 and 7 illustrate release curves of flavor from chewing gum.

FIG. 5 discloses a further variation of the embodiment in FIG. 4. Here the second compartment 22 comprises flavor-containing pellets with different flavors, namely e.g. pellets with spearmint flavor 24, pellets with orange flavor 25 and pellets with cinnamon flavor 26.

The embodiment of FIGS. 4 and 5 may of course be varied within the scope of the present invention, for example further compartments may be used, each of which could comprise different flavored pellets.

Chewing gum to be used with the present invention typically comprises a gum base portion, which is retained in the mouth throughout the chew.

The gum base is the masticatory substance of the chewing gum, which imparts the chew characteristics to the final product. The gum base typically defines the release profile of API, flavors and sweeteners and plays a significant role in the gum product.

The gum base may be processed into granules and together with other ingredients be compressed into a compressed chewing gum tablet according to methods known in the art.

The insoluble portion of the gum typically may contain any combination of elastomers, vinyl polymers, elastomer plasticizers, waxes, softeners, fillers and other optional ingredients such as colorants and antioxidants.

The elastomer compounds may be of natural origin or of synthetic origin, for example synthetic polyesters.

It is noted that the gum base may also include components typically referred to as chewing gum ingredients.

The chewing gum may, according to embodiments of the invention, comprise conventionally non-biodegradable polymers, such as natural resins, synthetic resins and/or synthetic or natural elastomers.

According to an embodiment of the invention, at least a part of the polymers of the chewing gum are biodegradable.

In embodiments of the invention, the piece of chewing gum may comprise combinations of biodegradable polymers and polymers generally regarded as non-biodegradable such as natural resins, synthetic resins and/or synthetic/natural elastomers. Likewise in embodiments where the flavor-containing formulation comprises gum base, this gum base may comprise the here-mentioned polymers.

The composition of gum base formulations can vary substantially depending on the particular product to be prepared and on the desired masticatory and other sensory characteristics of the final product. However, typical ranges of the above gum base components are: 5 to 80% by weight of elastomeric compounds, 5 to 80% by weight of elastomer plasticizers, 0 to 40% by weight of waxes, 5 to 35% by weight of softener, 0 to 50% by weight of filler, and 0 to 5% by weight of miscellaneous ingredients such as antioxidants, colorants, etc. The gum base may comprise about 5 to about 95% by weight of the chewing gum, more commonly; the gum base comprises 10 to about 60% by weight of the gum.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in gum base. This may be important when one wants to provide more elastomeric chain exposure to the alkanic chains of the waxes.

If desired, conventional elastomers or resins may be supplemented or substituted by biodegradable polymers.

Biodegradable polymers that may be used in the chewing gum of the present invention may be homopolymers, copolymers or terpolymers, including graft- and block-polymers.

A water-soluble portion of the chewing gum may include bulk sweeteners, high-intensity sweeteners, flavoring agents, softeners, emulsifiers, colors, acidulants, buffering agents, fillers, antioxidants, and other components that provide desired attributes.

Combinations of sugar and/or non-sugar sweeteners can be used in the chewing gum formulation processed in accordance with the invention. Additionally, the softener may also provide additional sweetness such as aqueous sugar or alditol solutions.

Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomalt, erythritol, lactitol and the like, alone or in combination.

High-intensity artificial sweetening agents can also be used alone or in combination with the above sweeteners. Preferred high-intensity sweeteners include, but are not limited to sucralose, aspartame, salts of acesulfame, alitame, neotame, twinsweet, saccharin and its salts, cyclamic acid and its salts, glycyrrhizin, dihydrochalcones, thaumatin, monellin, stevioside and the like, alone or in combination. In order to provide longer lasting sweetness and flavor perception, it may be desirable to encapsulate or otherwise control the release of at least a portion of the artificial sweetener. Techniques such as wet granulation, wax granulation, spray drying, spray chilling, fluid bed coating, coaservation, encapsulation in yeast cells and fiber extrusion may be used to achieve the desired release characteristics. Encapsulation of sweetening agents can also be provided using another chewing gum component such as a resinous compound.

Usage levels of the high-intensity artificial sweetener will vary considerably and will depend on factors such as potency of the sweetener, rate of release, desired sweetness of the product, level and type of flavor used and cost considerations. Thus, the active level of high-potency artificial sweetener may vary from about 0 to about 8% by weight, preferably 0.001 to about 5% by weight. When carriers used for encapsulation are included, the usage level of the encapsulated sweetener will be proportionately higher.

If a low-calorie gum is desired, a low-caloric bulking agent can be used. Examples of low caloric bulking agents include polydextrose, Raftilose, Raftilin, fructooligosaccharides (NutraFlora®), palatinose oligosaccharides; guar gum hydrolysates (e.g. Sun Fiber®) or indigestible dextrins (e.g. Fibersol®). However, other low-calorie bulking agents can be used.

The chewing gum according to the present invention may contain aroma agents and flavoring agents including natural and synthetic flavorings e.g. in the form of natural vegetable components, essential oils, essences, extracts, powders, including acids and other substances capable of affecting the taste profile. Examples of liquid and powdered flavorings include coconut, cola, green tea, coffee, chocolate, vanilla, grape fruit, cranberry, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, tea tree oil, and oils of the fruits mentioned above.

The chewing gum flavor may be a natural flavoring agent, which is freeze-dried, preferably in the form of a powder, slices or pieces or combinations thereof. The particle size may be less than 3 mm, less than 2 mm or more preferred less than 1 mm, calculated as the longest dimension of the particle. The natural flavoring agent may be in a form where the particle size is from about 3 μm to 2 mm, such as from 4 μm to 1 mm. Preferred natural flavoring agents include seeds from fruit e.g. from strawberry, blackberry and raspberry.

Various synthetic flavors, such as mixed fruit flavors may also be used in the present chewing gum cores. As indicated above, the aroma agent may be used in quantities smaller than those conventionally used. The aroma agents and/or flavors may be used in the amount from 0.01 to about 30% by weight of the final product depending on the desired intensity of the aroma and/or flavor used. Preferably, the content of aroma/flavor is in the range of 0.2 to 5%, more preferably 0.5 to 3%, by weight of the total composition.

In an embodiment of the invention, the flavoring agents comprise natural and synthetic flavorings in the form of natural vegetable components, essential oils, essences, extracts, powders, including acids and other substances capable of affecting the taste profile.

Active ingredients may advantageously be applied in a chewing gum according to the invention. Active ingredients generally refer to those ingredients that are included in a chewing gum composition for the desired end benefit they provide to the user. In some embodiments, active ingredients can include medicaments, nutrients, nutraceuticals, herbals, nutritional supplements, pharmaceuticals, drugs, and the like and combinations thereof. Moreover, in the present context, active ingredients may refer to flavor components, high intensity sweeteners or other taste establishing components.

Preferred active pharmaceutical ingredients (API) to be used in chewing gum according to embodiments of the invention are selected from the groups of antihistamines, antismoking agents, agents used for diabetes, decongestrants, peptides, pain-relieving agents, antacids, nausea-relieving agents, statines, antiobesity agents, dyspepsia agents, erectile dysfunction agents and other.

Most preferred API according to embodiments of the invention are cetirizine, levo cetirizine, nicotine, nicotine polacrilex, nicotine in combination with alkaline agents, metformin, metformin HCL, phenylephrine, GLP-1, exenatide, MC-4 receptor antagonist, PPY(3-36), deca-peptide, KSL-W (acetate), fluor, and chlorhexidine.

Also preferred API according to embodiments of the invention are loratadine, des-loratadine, nicotine bitartrate, nicotine in combination with caffeine, nicotine antagonists, combinations thereof or compounds comprising one or more of these, pseudoephedrine, flurbiprofen, paracetamol, acetylsalicylic acid, Ibuprofen, antacida, cimetidine, ranitidine, ondansetron, granisetron, metoclopramid, simvastatin, lovastatin, fluvastatin, acyclovir, benzydamin, rimonabant, varenicline, sildenafil, naltrexone, fluor in combination with fruit acids, derivatives, salts or isomers of chlorhexidine.

Some groups of suitable enhancers to e.g. enhance the uptake of API include bile salts, cetomacrogols, chelating agents, citrates, cyclodextrins, detergents, enamine derivatives, fatty acids, labrasol, lecithins, phospholipids, synthetic and natural surfactants, nonionic surfactants, cell envelope disordering compounds, solvents, steroidal detergents, chelators, solubilization agents, charge modifying agents, pH control agents, degradative enzyme inhibitors, mucolytic or mucus clearing agents.

Further groups of suitable enhancers include modulatory agents of epithelial junction physiology such as nitric oxide (NO) stimulators, chitosan, and chitosan derivatives; and vasodilator agents, selective transport-enhancing agents, stabilizing delivery vehicles, carriers, supports or complex-forming species with which exendins may be effectively combined, associated, contained, encapsulated or bound to stabilize an active agent for enhanced mucosal delivery; and membrane penetration-enhancing agents including surfactants, bile salts, phospholipid or fatty acid additives, mixed micelle, liposome, carrier, alcohol, enamine, NO donor compound, a long-chain amphipathic molecule, small hydrophobic penetration enhancer, sodium or a salicylic acid derivative, glycerol ester of acetoacetic acid, cyclodextrin or beta-cyclodextrin derivative, medium-chain fatty acid, chelating agent, amino acid or salt thereof, N-acetylamino acid or salt thereof, enzyme degradative to a selected membrane component, inhibitor of fatty acid synthesis, inhibitor of cholesterol synthesis, any combination of the membrane penetration enhancing agents.

Examples of enhancers suitable for application in chewing gum according to embodiments of the invention include cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-40 hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids ($C_8$-$C_{18}$) ethoxylated.

Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phosphatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil, Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, NOC5 [3-(2-hydroxy-1-(methyl-ethyl)-2-nitrosohydrazino)-1-propanamine], NOC12 [iV-ethyl-2-(1-ethyl-hydroxy-2-nitrosohydrazino)-ethanamine, SNAP [S-nitroso-N-acetyl-DL-penicillamine, NOR1, NOR4, deacylmethyl sulfoxide, azone, salicylamide, glyceryl-1,3-diacetoacetate, 1,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, and caproic acid, alkylsaccharide, fusidic acid, polyethylene glycol, cetyl alcohol, polyvinylpyrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropyl-β-cyclodetran, Sulfobutylether-β-cyclodextran, Methyl-β-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine, 1-O-alkyl-2-O-acetyl-sn-glycero-3-phospho(N,N,N-trimethyl) hexanolamine, propylene glycol, tetradecylmaltoside (TDM), sucrose dedecanoate.

Examples of suitable mucoadhesives as enhancers according to embodiments of the invention include Carbopol 934+HPC, Maize+Carbopol 907, HPC (hydroxypropyl cellulose), Na-CMC, HPMC (hydroxypropylmethylcellulose), HEMA hydroxyethyl metacrylate, Carbopol 907 crosslinked with sucrose, Polyacrylic acids (PAA), Chitosans, Lectins, Polymethacrylate derivatives, Hyaluronic acid, P(AA-co-PEG) monomethylether monomethacrylate, PAA-PVP (Poly acrylic acid-poly vinyl pyrrilidone), PVP-PEG, methylcellulose, N-Trimethyl Chitosans, PDMAEMA, poly(dimethylaminoethyl methacrylate), HEC Hydroxyethyl Cellulose, Carbomer 940, Carbomer 971, Polyethylene Oxide, Dextrin, Poly(Methyl Vinyl Ether/Maleic Anhydride), Polycarbophil that is polymers of acrylic acid crosslinked with divinyl glycol, PVP (PVP: Poly vinyl pyrrilidone), Agar, Tragacanth, Sodium Alginate, Karaya gum, MEC, HPC (HPC: Hydroxy propyl cellulose), Lectins, AB Block copolymer of oligo (methyl methacrylate) and PAA, Polymers with thiol groups, Spheromers, Thiomers, Alginic acid sodium salt, Carbopol 974P (Carbomer), EC (EC: Ethylcellulose), CMC (CMC: Carboxymethyl cellulose), Dextran, Guar Gum, Pectins, Starch, Gelatin, Casein, Acrylic acid polymers, Polymers of acrylic acid esters, Acrylic acid copolymers, Vinyl polymers, Vinyl copolymers, Polymers of Vinyl alcohols, Alcoxy polymers, polyethylene oxide polymers, and polyethers.

Some groups of suitable enhancers include solubilization agents; charge modifying agents; pH control agents; degradative enzyme inhibitors; modulatory agents of epithelial junction physiology, such as nitric oxide (NO) stimulators, chitosan, or chitosan derivatives; vasodilator agents; selective transport-enhancing agents; stabilizing delivery vehicles, carriers, supports or complex-forming species with which exendin(s) is/are effectively combined, associated, contained, encapsulated or bound to stabilize the active agent for enhanced mucosal delivery; small hydrophilic penetration enhancers; emulsifiers, mucolytic or mucus clearing agents; membrane penetration-enhancing agents such as e.g., (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule, (viii) a small hydrophobic penetration enhancer, (ix) sodium or a salicylic acid derivative, (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii)).

In various embodiments of the invention, exendin is combined with one, two, three, four or more of the mucosal delivery-enhancing agents recited above.

Some suitable enhancers for application according to the present invention include pH control agents selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

The suitable pH control agents suitable according to the present invention include buffers.

Examples of dry binders to be used according to embodiments of the invention include mikro-crystalline cellulose (MCC), silicified micro-crystalline cellulose (SMCC), spray dried lactose, fast flow lactose, anhydrous lactose, sucrose, mannitol, mannitol EZ, dextrose, fructose, sorbitol, povidone, copovidone, dicalcium phosphate (DCP), starch (corn, potato and rice), pre-gelatinized starch, or combinations thereof. A number of filler materials may furthermore be used as dry binders.

Active ingredients may be classified according to The Anatomical Therapeutic Chemical (ATC) classification system, which is a system for classification of medicinal products according to their primary constituent and to the organ or system on which they act and their chemical, pharmacological and therapeutic properties.

The first level of the ATC is split into 14 main groups based on the anatomical group:
A: Alimentary tract and metabolism
B: Blood and blood forming organs
C: Cardiovascular system
D: Dermatologicals
G: Genito urinary system and sex hormones
H: Systemic hormonal preparations, excl. sex hormones and insulins
J: Antiinfectives for systemic use
L: Antineoplastic and immunomodulating agents
M: Musculo-skeletal system
N: Nervous system
P: Antiparasitic products, insecticides and repellents
R: Respiratory system
S: Sensory organs
V: Various Further subdivision is done into a second, third, fourth and fifth sub-group, which is based on the therapeutic main group, the therapeutic/pharmacological subgroup, the chemical/therapeutic/pharmacological subgroup, and the chemical substance subgroup respectively. In this sense each active ingredient has been given a unique ATC identification code indicating where the active ingredient may be useful.

However, as some active ingredients are useful in more than one area, some of the active ingredients mentioned in this document belong to two or more of the mentioned groups, e.g. phenylephrine, which has an ATC identification code in both C, R, and S, i.e. both C01CA06, R01AA04, R01AB01, R01BA03, S01FB01, and S01GA05 are ATC identification codes identifying phenylephrine.

The following list discloses examples of active ingredients which can be classified according to the ATC classification mentioned above and which are active ingredients which may be used in a chewing gum according to embodiments of the invention:

Ephedrine, Magaldrate, Pseudoephedrine, Sildenafil, Xylocalne, Benzalconium chloride, Caffeine, Phenylephrine, Amfepramone, Orlistat, Sibutramine, Acetaminophen, Aspirin, Aluminum amino acetate, Aluminum amino acetate in combination with Magnesium oxide, Aluminum oxide hydrate in combination with Magnesiumoxide, Calcium carbonate in combination with Magnesium hydroxide, Calciumcarbonate, Dihydroxy Aluminum sodium carbonate, Magnesiumoxide, Glitazones, Metformin, Chlorpromazine, Dimenhydrinat, Domperidone, Meclozine, Metoclopramide, Odansetron, Prednisolone, Promethazine, Acrivastine, Cetirizine, Cinnarizine, Clemastine, Cyclizine, Desloratadine, Dexchlorpheniramine, Dimenhydrinate, Ebastine, Fexofenadine, Ibuprofen, Levolevoproricin, Loratadine, Meclozine, Mizolastine, Promethazine, Miconazole, Vitamin B12, Folic acid, Ferro compounds, vitamin C, Chlorhexidine diacetate, Fluoride, Decapeptide KSL, Aluminum fluoride, Aminochelated calcium, Ammonium fluoride, Ammonium fluorosilicate, Ammonium monofluorphosphate, Calcium fluoride, Calcium gluconate, Calcium glycerophosphate, Calcium lactate, Calcium monofluorphosphate, Calciumcarbonate, Carbamide, Cetyl pyridinium chloride, Chlorhexidine, Chlorhexidine digluconate, Chlorhexidine Chloride, Chlorhexidine diacetate, CPP Caseine Phospho Peptide, Hexetedine, Octadecentyl Ammonium fluoride, Potasium fluorosilicate, Potassium Chloride, Potassium monofluorphosphate, Sodium bi carbonate, Sodium carbonate, Sodium fluoride, Sodium fluorosilicate, Sodium monofluorphosphate, Sodium tri polyphosphate, Stannous fluoride, Stearyl Trihydroxyethyl Propylenediamine Dihydrofluoride, Strontium chloride, Tetra potassium pyrophosphate, Tetra sodium pyrophosphate, Tripotassium orthophosphate, Trisodium orthophosphate, Alginic acid, Aluminum hydroxide, Sodium bicarbonate, Sildenafil, Tadalafil, Vardenafil, Yohimbine, Cimetidine, Nizatidine, Ranitidine, Acetylsalicylic acid, Clopidogrel, Acetylcysteine, Bromhexine, Codeine, Dextromethorphan, Diphenhydramine, Noscapine, Phenylpropanolamine, vitamin D, Simvastatin, Bisacodyl, Lactitol, Lactulose, Magnesium oxide, Sodium picosulfate, Senna glycosides, Benzocaine, Lidocaine, Tetracaine, Almotriptan, Eletriptan, Naratriptan, Rizatriptan, Sumatriptan, Zolmitriptan, Calcium, Chromium, Copper, Iodine, Iron, Magnesium, Manganese, Molybdenium, Phosphor, Selenium, Zinc, Nicotine, Nicotine bitartrate, Nicotine pftalate, Nicotine polacrilex, Nicotine sulphate, Nicotine tartrate, Nicotine citrate, Nicotine lactate, Chloramine, Hydrogenperoxide, Metronidazole, Triamcinolonacetonide, Benzethonium Chl., Cetyl pyrid. Chl., Chlorhexidine, Fluoride, Lidocaine, Amphotericin, Miconazole, Nystatin, Fish oil, Ginkgo Biloba, Ginseng, Ginger, Purple coneflower, Saw Palmetto, Cetirizine, Levocetirizine, Loratadine, Diclofenac, Flurbiprofen, Acrivastine Pseudoephedrine, Loratadine Pseudoephedrine, Glucosamine, hyaluronic acid, Decapeptide KSL-W, Decapeptide KSL, Resveratrol, Misoprostol, Bupropion, Nicotine, Ondansetron HCl, Esomeprazole, Lansoprazole, Omeprazole, Pantoprazole, Rabeprazole, Bacteria and the like, Loperamide, Simethicone, Acetylsalicylic acid and others, Sucralfate, Vitamin A, Vitamin B1, Vitamin B12, Vitamin B2, Vitamin B6, Biotin, Vitamin C, Vitamin D, Vitamin E, Folinic acid, Vitamin K, Niacin, Q10, Clotrimazole, Fluconazole, Itraconazole, Ketoconazole, Terbinafine, Allopurinol, Probenecid, Atorvastatin, Fluvastatin, Lovastatin, Nicotinic acid, Pravastatin, Rosuvastatin, Simvastatin, Pilocarpine, Naproxen, Alendronate, Etidronate, Raloxifene, Risedronate, Benzodiazepines, Disulfuram, Naltrexone, Buprenorphine, Codeine, Dextropropoxyphene, Fentanyl, Hydromorphone, Ketobemidone, Ketoprofen, Methadone, Morphine, Naproxen, Nicomorphine, Oxycodone, Pethidine, Tramadol, Amoxicillin, Ampicillin, Azithromycin, Ciprofloxacin, Clarithromycin, Doxycyclin, Erythromycin, Fusidic acid, Lymecycline, Metronidazole, Moxifloxacin, Ofloxacin, Oxytetracycline, Phenoxymethylpenicillin, Rifamycins, Roxithromycin, Sulfamethizole, Tetracycline, Trimethoprim, Vancomycin, Acarbose, Glibenclamide, Gliclazide, Glimepiride, Glipizide, Insulin, Repaglinide, Tolbutamide, Oseltamivir, Aciclovir, Famciclovir, Penciclovir, Valganciclovir, Amlopidine, Diltiazem, Felodipine, Nifedipine, Verapamil, Finasteride, Minoxidil, Cocaine, Buphrenorphin, Clonidine, Methadone, Naltrexone, Calciumantagonists, Clonidine, Ergotamine, β-blockers, Aceclofenac, Celecoxib, Dexiprofen, Etodolac, Indometacin, Ketoprofen, Ketorolac, Lornoxicam, Meloxicam, Nabumetone, Oiroxicam, Parecoxib, Phenylbutazone, Piroxicam, Tiaprofenic acid, Tolfenamic acid, Aripiprazole, Chlorpromazine, Chlorprothixene, Clozapine, Flupentixol, Fluphenazine, Haloperidol, Lithium carbonate, Lithium citrate, Melperone, Penfluridol, Periciazine, Perphenazine, Pimozide, Pipamperone, Prochlorperazine, Risperidone, Thioridizin, Fluconazole, Itraconazole, Ketoconazole, Voriconazole, Opium, Benzodiazepines, Hydroxine, Meprobamate, Phenothiazine, Aluminumaminoacetate, Esomeprazole, Famotidine, Magnesium oxide, Nizatide, Omeprazole, Pantoprazole, Fluconazole, Itraconazole, Ketoconazole, Metronidazole, Amphetamine, Atenolol, Bisoprolol fumarate, Metoprolol, Metropolol, Pindolol, Propranolol, Auranofin, and Bendazac.

Further examples of useful active ingredients include active ingredients selected from the therapeutical groups comprising: Analgesic, Anaestetic, Antipyretic, Anti allergic, Anti-arrytmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestrant, Gastro-intestinal sedative, Sexual dysfunction agent, Desinfectants, Anti-diarrheal, Anti-anginal substance, Vasodilator, Anti-hypertensive agent, Vasoconstrictor, Migraine treating agent, Antibiotic, Tranquilizer, Ntipsychotic, Anti-tumor drug, Anticoagulant, Antithrombotic agent, Hypnotic, Sedative, Anti-emetic, Anti-nauseant, Anticonvulsant, Neuromuscular agent, Hyper and hypoglycaemic, Thyroid and antithyroid, Diuretic, Antispasmodic, Uterine relaxant, Anti-obesity agent, Anoretic, Spasnolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretic, Anti-flatulent, Betablocker, Teeth Whitener, Enzyme, Co-enzyme, Protein, Energy booster, Fiber, Probiotics, Prebiotics, Antimicrobial agent, NSAID, Anti-tussives, Decongestrants, Anti-histamines, Expectorants, Anti-diarrheals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, and Sexual dysfunction agents.

Examples of useful active ingredients include: Casein glyco-macro-peptide (CGMP), Nicotine, Nicotine bitartrate, Nicotine sulphate, Nicotine tartrate, Nicotine pftalate, Nicotine lactate, Nicotine citrate, Nicotine polacrilex, Triclosan, Cetyl pyridinium chloride, Domiphen bromide, Quarternary ammonium salts, Zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniramine-maleate, Carbinoxamine maleate, Clemastine fumarate, Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbrompheniamine, Guaifenesin, Ipecac, Potassium iodide, Terpin hydrate, Loperamide, Famotidine, Ranitidine, Omeprazole, Lansoprazole, Aliphatic alcohols, Barbiturates, Caffeine, Nicotine, Strychnine, Picrotoxin, Pentyenetetrazol, Phenyhydantoin, Phenobarbital, Primidone, Carbamazepine, Etoxsuximide, Methsuximide, Phensuximide, Trimethadione, Diazepam, Benzodiazepines, Phenacemide, Pheneturide, Acetazolamide, Sulthiame, Bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, Imipramine, Tranylcypromine, Phenelzine, Lithium, Sildenafil citrate, Tadalafil, and Vardenafil CL, Tibolon, Rimonabant, Allergens, Sitagliptin, Benzydamin, Tesofensine, Tapentadol, and Acamprosate.

Examples of useful active peptides and obesity ingredients include: Sibutrami, Amfepramon, Orlistat, Rimonabant, Metformin, 869682 (GSK), AVE1625 (Sanofi Aventis), Cetilistat, Contrave, CP-945,598—Pfizer, Empatic—Orexigen Therapeutics, KRP-204—Kyorin, Liraglutide, Lorcaserin, OBE101 (OBEcure), Obineptide, Pramlitide, Pramlitide combination therap., PYY3-36 (Nastech), Qnexa, S-2367 (Shionogi), SLV319 (Solvay/BMS), Taranabant, Tesofensine, TM30339 (7™ Pharma), RHS08 (Rheoscience), Byetta (exenatide), glucagon-like peptide-2 (GLP-2), Glucagon-like peptide-1 derivatives, ZP-10 (Zealand Pharma), Vasopressin, a vasopressin polypeptide analog, Desmopressin, Glucagon, Corticotropin, Gonadotropin, C-peptide of insulin, Parathyroid hormone, Human growth hormone, Growth hormone, Growth hormone releasing hormone, Oxytocin, Corticotropin releasing hormone, Somatostatin, a somatostatin polypeptide analog, Gonadotropin agonist, a gonadotropin agonist polypeptide analog, atrial natriuretic peptide, Thyroxine releasing hormone, follicle stimulating hormone, Prolactin, a growth factor, Interleukin, polypeptide vaccine, enzyme, endorphin, glycoprotein, lipoprotein, a polypeptide involved in the blood coagulation cascade, peptide YY (PYY), parathyroid hormone (PTH), interferon-alpha (INF-.alpha.), interferon-beta (INF-.beta.), interferon-gamma (INF-.gamma.), oxytocin, insulin and carbetocin. ALK oral product, ALK product, Grazax, Decapeptide KSL, Decapaptide KSL-W, Decapeptide KSL in combination with cetylpyridinium chloride, Decapaptide KSL-W in combination with cetylpyridinium chloride, Amylin, Amylin derivater, Amylin analoger, Symlin, αMSH, αMSH derivater, aMSH analoger Examples of useful active ingredients include active ingredients selected from the groups of ace-inhibitors, antianginal drugs, anti-arrhythmias, anti-asthmatics, anti-cholesterolemics, analgesics, anesthetics, anticonvulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocriptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of active ingredients contemplated for use in the present invention can include antacids, H2-antagonists, and analgesics. For example, antacid dosages can be prepared using the ingredients calcium carbonate alone or in combination with magnesium hydroxide, and/or aluminum hydroxide. Moreover, antacids can be used in combination with H2-antagonists.

Analgesics include opiates and opiate derivatives, such as Oxycontin™, ibuprofen, aspirin, acetaminophen, and combinations thereof that may optionally include caffeine.

Other drug active ingredients for use in embodiments can include anti-diarrheals such as Immodium™ AD, anti-histamines, anti-tussives, decongestants, vitamins, and breath fresheners. Also contemplated for use herein are anxiolytics such as Xanax™; anti-psychotics such as Clozaril™ and Haldol™; non-steroidal anti-inflammatories (NSAID's) such as ibuprofen, naproxen sodium, Voltaren™ and Lodine™, anti-histamines such as Claritin™, Hismanal™, Relafen™, and Tavist™; antiemetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™, and CaH-antagonists such as Procardia™, Adalat™, and Calan™.

The popular H2-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients can include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts. A variety of nutritional supplements may also be used as active ingredients including virtually any vitamin or mineral. For example, vitamin A, vitamin C, vitamin D, vitamin E, vitamin K, vitamin B6, vitamin B12, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used. Examples of nutritional supplements that can be used as active ingredients are set forth in U.S. Patent Application Publication Nos. 2003/0157213 Al, 2003/0206993 and 2003/0099741 Al which are incorporated in their entirety herein by reference for all purposes. Various herbals may also be used as active ingredients such as those with various medicinal or dietary supplement properties. Herbals are generally aromatic plants or plant parts and or extracts thereof that can be used medicinally or for flavoring. Suitable herbals can be used singly or in various mixtures. Commonly used herbs include Echinacea, Goldenseal, Calendula, Rosemary, Thyme, Kava Kava, Aloe, Blood Root, Grapefruit Seed Extract, Black Cohosh, Ginseng, Guarana, Cranberry, Ginko Biloba, St. John's Wort, Evening Primrose Oil, Yohimbe Bark, Green Tea, Ma Huang, Maca, Bilberry, Lutein, and combinations thereof.

Especially when hydrophilic, encapsulation of the active ingredient will result in a delay in the release of the predominant amount of the active ingredient during consumption of a chewing gum that includes the encapsulated active ingredient (e.g., as part of a delivery system added as an ingredient to the chewing gum), in some embodiments, the release profile of the ingredient (e.g., the active ingredient) can be managed for a chewing gum by managing various characteristics of the ingredient, delivery system containing the ingredient, and/or the chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more components of an effervescing system are managed for a chewing gum. The effervescent system may include one or more edible acids and one or more edible alkaline materials. The edible acid(s) and the edible alkaline material(s) may react together to generate effervescence. In some embodiments, the alkaline material(s) may be selected from, but is not limited to, alkali metal carbonates, alkali metal bicarbonates, alkaline earth metal carbonates, alkaline earth metal bicarbonates, and combinations thereof. The edible acid(s) may be selected from, but is not limited to, citric acid, phosphoric acid, tartaric acid, malic acid, ascorbic acid, and combinations thereof. In some embodiments, an effervescing system may include one or more other ingredients such as, for example, carbon dioxide, oral care ingredients, flavorants, etc.

For examples of use of an effervescing system in a chewing gum, refer to U.S. Provisional Patent No. 60/618,222 filed Oct. 13, 2004, and entitled "Effervescent Pressed Gum Tablet Compositions," the contents of which are incorporated herein by reference for all purposes. Other examples can be found in U.S. Pat. No. 6,235,318, the contents of which are incorporated herein by reference for all purposes.

In some embodiments, the release profiles of one or more appetite suppressors are managed for a chewing gum. Appetite suppressors can be ingredients such as fiber and protein that function to depress the desire to consume food. Appetite suppressors can also include benzphetamine, diethylpropion, mazindol, phendimetrazine, phentermine, hoodia (P57), Olibra™, ephedra, caffeine and combinations thereof. Appetite suppressors are also known by the following trade names: Adipex™ Adipost™, Bontril™ PDM, Bontril™ Slow Release, Didrex™, Fastin™, Ionamin™, Mazanor™, Melfiat™, Obenix™, Phendiet™, Phendiet-105™, Phentercot™, Phentride™, Plegine™, Prelu-2™, Pro-Fast™, PT 105™, Sanorex™, Tenuate™, Sanorex™, Tenuate™, Tenuate Dospan™, Tepanil Ten-Tab™, Teramine™, and Zantryl™. These and other suitable appetite suppressors are further described in the following U.S. patents, all of which are incorporated in their entirety by reference hereto: U.S. Pat. No. 6,838,431 to Portman, U.S. Pat. No. 6,716,815 to Portman, U.S. Pat. No. 6,558,690 to Portman, U.S. Pat. No. 6,468,962 to Portman, U.S. Pat. No. 6,436,899 to Portman.

In some embodiments, the release profiles of one or more breath fresheners are managed for a chewing gum. Breath fresheners can include essential oils as well as various aldehydes, alcohols, and similar materials. In some embodiments, essential oils can include oils of spearmint, peppermint, wintergreen, sassafras, chlorophyll, citral, geraniol, cardamom, clove, sage, carvacrol, eucalyptus, cardamom, magnolia bark extract, marjoram, cinnamon, lemon, lime, grapefruit, and orange. In some embodiments, aldehydes such as cinnamic aldehyde and salicylaldehyde can be used. Additionally, chemicals such as menthol, carvone, iso-garrigol, and anethole can function as breath fresheners. Of these, the most commonly employed are oils of peppermint, spearmint and chlorophyll.

In addition to essential oils and chemicals derived from them, in some embodiments, breath fresheners can include but are not limited to zinc citrate, zinc acetate, zinc fluoride, zinc ammonium sulfate, zinc bromide, zinc iodide, zinc chloride, zinc nitrate, zinc fluorosilicate, zinc gluconate, zinc tartarate, zinc succinate, zinc formate, zinc chromate, zinc phenol sulfonate, zinc dithionate, zinc sulfate, silver nitrate, zinc salicylate, zinc glycerophosphate, copper nitrate, chlorophyll, copper chlorophyll, chlorophyllin, hydrogenated cottonseed oil, chlorine dioxide, beta cyclodextrin, zeolite, silica-based materials, carbon-based materials, enzymes such as laccase, and combinations thereof. In some embodiments, the release profiles of probiotics can be managed for a compressible gum including, but not limited to lactic acid producing microorganisms such as *Bacillus coagulans, Bacillus subtilis, Bacillus laterosporus, Bacillus laevolacticus, Sporolactobacillus inulinus, Lactobacillus acidophilus, Lactobacillus curvatus, Lactobacillus plantarum, Lactobacillus jenseni, Lactobacillus casei, Lactobacillus fermentum, Lactococcus lactis, Pedioccocus acidilacti, Pedioccocus pentosaceus, Pedioccocus urinae, Leuconostoc mesenteroides, Bacillus coagulans, Bacillus subtilis, Bacillus laterosporus, Bacillus laevolacticus, Sporolactobacillus inulinus* and mixtures thereof. Breath fresheners are also known by the following trade names: Retsyn™, Actizol™, and Nutrazin™. Examples of malodor-controlling compositions are also included in U.S. Pat. No. 5,300,305 to Stapler et al. and in U.S. Patent Application Publication Nos. 2003/0215417 and 2004/0081713 which are incorporated in their entirety herein by reference for all purposes.

In some embodiments, the release profiles of one or more dental care ingredients may be managed for a chewing gum. Such dental care ingredients (also known as oral care ingredients) may include but are not limited to tooth whiteners, stain removers, oral cleaning, bleaching agents, desensitizing agents, dental remineralization agents, antibacterial agents, anticaries agents, plaque acid buffering agents, surfactants and anticalculus agents. Non-limiting examples of such ingredients can include, hydrolytic agents including proteolytic enzymes, abrasives such as hydrated silica, calcium carbonate, sodium bicarbonate and alumina, other active stain-removing components such as surface-active agents, including, but not limited to anionic surfactants such as sodium stearate, sodium palminate, sulfated butyl oleate, sodium oleate, salts of fumaric acid, glycerol, hydroxylated lecithin, sodium lauryl sulfate and chelators such as polyphosphates, which are typically employed as tartar control ingredients. In some embodiments, dental care ingredients can also include tetrasodium pyrophosphate and sodium tripolyphosphate, sodium bicarbonate, sodium acid pyrophosphate, sodium tripolyphosphate, xylitol, sodium hexametaphosphate. In some embodiments, peroxides such as carbamide peroxide, calcium peroxide, magnesium peroxide, sodium peroxide, hydrogen peroxide, and peroxydiphospate are included. In some embodiments, potassium nitrate and potassium citrate are included. Other examples can include casein glycomacropeptide, calcium casein peptone-calcium phosphate, casein phosphopeptides, casein phosphopeptide-amorphous calcium phosphate (CPP-ACP), and amorphous calcium phosphate. Still other examples can include papaine, krillase, pepsin, trypsin, lysozyme, dextranase, mutanase, glycoamylase, amylase, glucose oxidase, and combinations thereof. Further examples can include surfactants such as sodium stearate, sodium ricinoleate, and sodium lauryl sulfate surfactants for use in some embodiments to achieve increased prophylactic action and to render the dental care ingredients more cosmetically acceptable. Surfactants can preferably be detersive materials which impart to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine. In addition to surfactants, dental care ingredients can include antibacterial agents such as, but not limited to, triclosan, chlorhexidine, zinc citrate, silver nitrate, copper, limonene, and cetyl pyridinium chloride. In some embodiments, additional anticaries agents can include fluoride ions or fluorine-providing components such as inorganic fluoride salts. In some embodiments, soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride can be included. In some embodiments, a fluorine-containing compound having a beneficial effect on the care and hygiene of the oral cavity, e.g., diminution of enamel solubility in acid and protection of the teeth against decay may also be included as an ingredient. Examples thereof include sodium fluoride, stannous fluoride, potassium fluoride, potassium stannous fluoride (SnF.sub.2-KF), sodium hexafluorostannate, stannous chlorofluoride, sodium fluorozirconate, and sodium monofluorophosphate. In some embodiments, urea is included. Further examples are included in the following U.S. patents and U.S. published patent applications, the contents of all of which are incorporated in their entirety herein by reference for all purposes: U.S. Pat. No. 5,227,154 to Reynolds, U.S. Pat. No. 5,378,131 to Greenberg, U.S. Pat. No. 6,846,500 to Luo et al, U.S. Pat. No. 6,733,818 to Luo et al., U.S. Pat. No. 6,696,044 to Luo et al., U.S. Pat. No. 6,685,916 to Holme et al., U.S. Pat. No. 6,485,739 to Luo et al., U.S. Pat. No. 6,479,071 to Holme et al., U.S. Pat. No. 6,471,945 to Luo et al., U.S. Patent Publication Nos. 20050025721 to Holme et al., 2005008732 to Gebreselassie et al., and 20040136928 to Holme et al.

In some embodiments, the release profiles of one or more flavor potentiators can be managed for a chewing gum. Flavor potentiators can consist of materials that may intensify, supplement, modify or enhance the taste and/or aroma perception of an original material without introducing a characteristic taste and/or aroma perception of their own. In some embodiments, potentiators designed to intensify, supplement, modify, or enhance the perception of flavor, sweetness, tartness, umami, kokumi, saltiness and combinations thereof can be included. In some embodiments, sweetness may be potentiated by the inclusion of monoammonium glycyrrhizinate, licorice glycyrrhizinates, citrus aurantium, maltol, ethyl maltol, vanilla, vanillin, and combinations thereof. In some embodiments, sugar acids, sodium chloride, potassium chloride, sodium acid sulfate, and combinations thereof may be included for flavor potentiation. In other examples, glutamates such as monosodium glutamate (MSG), monopotassium glutamate, hydrolyzed vegetable protein, hydrolyzed animal protein, yeast extract, and combinations thereof are included. Further examples can include glutathione, and nucleotides such as inosine monophosphate (IMP), disodium inosinate, xanthosine monophosphate, guanylate monophosphate (GMP), and combinations thereof. For bitterness blocking or taste masking, ingredients that interact with bitterness receptors to suppress bitterness or off tastes may be included. In some embodiments, adenosine monophosphate (AMP) can be included for bitterness suppression. Bitterness modification can also be accomplished by using sweetness or flavors with complementary bitter notes such as chocolate. Further examples of flavor potentiator compositions that impart kokumi are also included in U.S. Pat. No. 5,679,397 to Kuroda et al, the entire contents of which are incorporated in its entirety herein by reference.

Typically, encapsulation of a flavor potentiator will result in a delay in the release of the predominant amount of the flavor potentiator during consumption of a chewing gum that includes the encapsulated flavor potentiator (e.g., as part of a delivery system added as an ingredient to the chewing gum composition). In some embodiments, the release profile of the ingredient (e.g., the flavor potentiator) can be managed for a chewing gum by managing various characteristics of the ingredient, delivery system containing the ingredient, and/or the compressible chewing gum containing the delivery system and/or how the delivery system is made.

In some embodiments, the release profiles of one or more acids may be managed for a chewing gum. Acids can include, but are not limited to acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof.

Typically, encapsulation of a food acid will result in a delay in the release of the predominant amount of the active ingredient during consumption of a compressible chewing gum that includes the encapsulated food acid (e.g., as part of a delivery system added as an ingredient to the chewing gum).

In some embodiments, the release profiles of one or more micronutrients can be managed for a chewing gum. Micronutrients can include materials that have an impact on the nutritional wellbeing of an organism even though the quantity required by the organism to have the desired effect is small relative to macronutrients such as protein, carbohydrate, and fat. Micronutrients can include, but are not limited to vitamins, minerals, enzymes, phytochemicals, antioxidants, and combinations thereof. In some embodiments, vitamins can include fat soluble vitamins such as vitamin A, vitamin D, vitamin E, and vitamin K and combinations thereof, in some embodiments, vitamins can include water soluble vitamins such as vitamin C (ascorbic acid), the B vitamins (thiamine or B1, riboflavoin or B2, niacin or B3, pyridoxine or B6, folic acid or B9, cyanocobalimin or B12, pantothenic acid, biotin), and combinations thereof.

In some embodiments, minerals can include but are not limited to sodium, magnesium, chromium, iodine, iron, manganese, calcium, copper, fluoride, potassium, phosphorous, molybdenum, selenium, zinc, and combinations thereof.

In some embodiments micronutrients can include but are not limited to L-carnitine, choline, coenzyme Q10, alphalipoic acid, omega-3-fatty acids, pepsin, phytase, trypsin, lipases, proteases, cellulases and combinations thereof.

Antioxidants can include materials that scavenge free radicals. In some embodiments, antioxidants can include but are not limited to ascorbic acid, citric acid, rosemary oil, vitamin A, vitamin E, vitamin E phosphate, tocopherols, di-alphatocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

In some embodiments, phytochemicals can include but are not limited to cartotenoids, chlorophyll, chlorophyllin, fiber, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, sterols, stanols, stanol esters, sterol esters and combinations thereof.

Typically, encapsulation of the micronutrient will result in a delay in the release of the predominant amount of the active ingredient during consumption of a chewing gum that includes the encapsulated micronutrient (e.g., as part of a delivery system added as an ingredient to the chewing gum).

In some embodiments, the release profiles of one or more mouth moisteners can be managed for a compressible gum. Mouth moisteners can include, but are not limited to, saliva stimulators such as acids and salts and combinations thereof. In some embodiments, acids can include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof. Mouth moisteners can also include hydrocolloid materials that hydrate and may adhere to oral surface to provide a sensation of mouth moistening. Hydrocolloid materials can include naturally occurring materials such as plant exudates, seed gums, and seaweed extracts or they can be chemically modified materials such as cellulose, starch, or natural gum derivatives. In some embodiments, hydrocolloid materials can include pectin, gum arabic, acacia gum, alginates, agar, carageenans, guar gum, xanthan gum, locust bean gum, gelatin, gellan gum, galactomannans, tragacanth gum, karaya gum, curdlan, konjac, chitosan, xyloglucan, beta glucan, furcellaran, gum ghatti, tamarin, bacterial gums, and combinations thereof. Additionally, in some embodiments, modified natural gums such as propylene glycol alginate, carboxymethyl locust bean gum, low methoxyl pectin, and their combinations can be included. In some embodiments, modified celluloses can be included such as microcrystalline cellulose, carboxymethylcellulose (CMC), methylcellulose (MC), hydroxypropylmethylcellulose (HPMC), and hydroxypropylcellulose (MPC), and combinations thereof. Similarly, humectants which can provide a perception of mouth hydration can be included. Such humectants can include, but are not limited to glycerol, sorbitol, polyethylene glycol, erythritol, and xylitol. Additionally, in some embodiments, fats can provide a perception of mouth moistening. Such fats can include medium chain triglycerides, vegetable oils, fish oils, mineral oils, and combinations thereof. Typically, encapsulation of a mouth moistening agent will result in a delay in the release of the predominant amount of the active ingredient during consumption of a chewing gum that includes the encapsulated mouth moistening agent (e.g., as part of a delivery system added as an ingredient to the compressible chewing gum). In some embodiments, the release profile of the ingredient (e.g., the mouth moistening agent) can be managed for a compressible gum by managing various characteristics of the ingredient, delivery system containing the ingredient, and/or the compressible chewing gum containing the delivery system and/or how the delivery system is made.

In some embodiments, the release profiles of one or more ingredients that soothe the throat can be managed for a chewing gum. Throat soothing ingredients can include analgesics, anesthetics, demulcents, antiseptic, and combinations thereof. In some embodiments, analgesics/anesthetics can include menthol, phenol, hexylresorcinol, benzocaine, dyclonine hydrochloride, benzyl alcohol, salicyl alcohol, and combinations thereof. In some embodiments, demulcents can include but are not limited to slippery elm bark, pectin, gelatin, and combinations thereof. In some embodiments, antiseptic ingredients can include cetylpyridinium chloride, domiphen bromide, dequalinium chloride, and combinations thereof.

In some embodiments, antitussive ingredients such as chlophedianol hydrochloride, codeine, codeine phosphate, codeine sulfate, dextromethorphan, dextromethorphan hydrobromide, diphenhydramine citrate, and diphenhydramine hydrochloride, and combinations thereof can be included.

In some embodiments, throat soothing agents such as honey, propolis, aloe vera, glycerine, menthol and combinations thereof can be included. In still other embodiments, cough suppressants can be included. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants). In some embodiments, ingredients from either or both groups can be included.

In still other embodiments, antitussives can include, but are not limited to, the group consisting of codeine, dextromethorphan, dextrorphan, diphenhydramine, hydrocodone, noscapine, oxycodone, pentoxyverine and combinations thereof. In some embodiments, antihistamines can include, but are not limited to, acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, non-sedating antihistamines can include, but are not limited to, astemizole, cetirizine, ebastine, fexofenadine, loratidine, terfenadine, and combinations thereof.

In some embodiments, expectorants can include, but are not limited to, ammonium chloride, guaifenesin, ipecac fluid extract, potassium iodide and combinations thereof. In some embodiments, mucolytics can include, but are not limited to, acetylcycsteine, ambroxol, bromhexine and combinations thereof. In some embodiments, analgesic, antipyretic and anti-inflammatory agents can include, but are not limited to, acetaminophen, aspirin, diclofenac, diflunisal, etodolac, fenoprofen, flurbiprofen, ibuprofen, ketoprofen, ketorolac, nabumetone, naproxen, piroxicam, caffeine and mixtures thereof. In some embodiments, local anesthetics can include, but are not limited to, lidocaine, benzocaine, phenol, dyclonine, benzonotate and mixtures thereof. In some embodiments nasal decongestants and ingredients that provide the perception of nasal clearing can be included. In some embodiments, nasal decongestants can include but are not limited to phenylpropanolamine, pseudoephedrine, ephedrine, phenylephrine, oxymetazoline, and combinations thereof. In some embodiments ingredients that provide a perception of nasal clearing can include but are not limited to menthol, camphor, borneol, ephedrine, eucalyptus oil, peppermint oil, methyl salicylate, bornyl acetate, lavender oil, wasabi extracts, horseradish extracts, and combinations thereof. In some embodiments, a perception of nasal clearing can be provided by odoriferous essential oils, extracts from woods, gums, flowers and other botanicals, resins, animal secretions, and synthetic aromatic materials.

Typically, encapsulation of a throat care agent will result in a delay in the release of the predominant amount of the active ingredient during consumption of a compressible chewing gum that includes the encapsulated throat care agent (e.g. as part of a delivery system added as an ingredient to the compressible chewing gum).

In some embodiments, one or more colors can be included. As classified by the United States Food, Drug, and Cosmetic Act (21 C.F.R. 73), colors can include exempt from certification colors (sometimes referred to as natural even though they can be synthetically manufactured) and certified colors (sometimes referred to as artificial), or combinations thereof. In some embodiments, exempt from certification or natural colors can include, but are not limited to annatto extract, (E 160b), bixin, norbixin, astaxanthin, dehydrated beets (beet powder), beetroot red/betanin (E 162), ultramarine blue, canthaxanthin (E161g), cryptoxanthin (E161c), rubixanthin (E161d), violanxanthin (E161e), rhodoxanthin (E161f), caramel (E150(a-d)), β-apo-8'-carotenal (E160e), β-carotene (E160a), alpha carotene, gamma carotene, ethyl ester of beta-apo-8 carotenal (E160f), fiavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), haematococcus algae meal, synthetic iron oxide, iron oxides and hydroxides (E172), fruit juice, vegetable juice, dried algae meal, tagetes (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorbin (E160c), lycopene (E160d), and combinations thereof.

In some embodiments, certified colors can include, but are not limited to, FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminum (E173), silver (E174), gold (E175), pigment rubine/lithol rubine BK (E180), calcium carbonate (E170), carbon black (E153), black PN/brilliant black BN (E151), green S/acid brilliant green BS (E142), and combinations thereof. In some embodiments, certified colors can include FD&C aluminum lakes. These consist of the aluminum salts of FD&C dyes extended on an insoluble substrate of alumina hydrate. Additionally, in some embodiments, certified colors can be included as calcium salts.

Typically, encapsulation of a color will result in a delay in the release of the predominant amount of the active ingredient during consumption of a chewing gum that includes the encapsulated color (e.g., as part of a delivery system added as an ingredient to the compressible chewing gum).

In some embodiments, a delivery system or chewing gum may include two or more ingredients for which managed release from the compressible chewing gum during consumption of the compressible chewing gum is desired. In some embodiments, the ingredients may be encapsulated or otherwise included separately in different delivery systems. Alternatively, in some embodiments the ingredients may be encapsulated or otherwise included in the same delivery system. As another possibility, one or more of the ingredients may be free (e.g. unencapsulated) while one or more other ingredients may be encapsulated. A chewing gum may include a group of ingredients for which managed release of the group during consumption of the chewing gum is desired. Groups of two or more ingredients for which managed release from a chewing gum during consumption of the chewing gum may be desired include, but are not limited to: color and flavor, multiple flavors, multiple colors, cooling agent and flavor, warming agent and flavor, cooling agent and warming agent, cooling agent and high-intensity sweetener, warming agent and high-intensity sweetener, multiple cooling agents (e.g., WS-3 and WS-23, WS-3 and menthyl succinate), menthol and one or more cooling agents, menthol and one or more warming agents, multiple warming agents, high-intensity sweetener(s) and tooth whitening active(s), high-intensity sweetener(s) and breath-freshening active(s), an ingredient with some bitterness and a bitterness suppressor for the ingredient, multiple high-intensity sweeteners (e.g., acesulfame-k and aspartame), multiple tooth whitening active ingredients (e.g., an abrasive ingredient and an antimicrobial ingredient, a peroxide and a nitrate), a warming agent and a polyol, a cooling agent and a polyol, multiple polyols, a warming agent and micronutrient, a cooling agent and a micronutrient, a warming agent and a mouth moistening agent, a cooling agent and a mouth moistening agent, a warming agent and a throat care agent, a cooling agent and a throat care agent, a warming agent and a food acid, a cooling agent and food acid, a warming agent and an emulsifier/surfactant, a cooling agent and an emulsifier/surfactant, a warming agent and a color, a cooling agent and a color, a warming agent and a flavor potentiator, a cooling agent and a flavor potentiator, a warming agent with sweetness potentiator, a cooling agent with a sweetness potentiator, a warming agent and an appetite suppressant, a cooling agent and an appetite suppressant, a high-intensity sweetener and a flavor, a cooling agent and a teeth-whitening agent, a warming agent and a teeth-whitening agent, a warming agent and breath-freshening agent, a cooling agent and a breath-freshening agent, a cooling agent and an effervescing system, a warming agent and an effervescing system, a warming agent and an antimicrobial agent, a cooling agent and an antimicrobial agent, multiple anticalciums ingredients, multiple remineralization ingredients, multiple surfactants, remineralization ingredients with demineralization ingredients, acidic ingredients with acid buffering ingredients, anticalculus ingredients with antibacterial ingredients, remineralization ingredients with anticalculus ingredients, anticalculus ingredients with remineralization ingredients with antibacterial ingredients, surfactant ingredients with anticalculus ingredients, surfactant ingredients with antibacterial ingredients, surfactant ingredients with remineralization ingredients, surfactants with anticalculus ingredients with antibacterial ingredients, multiple types of vitamins or minerals, multiple micronutrients, multiple acids, multiple antimicrobial ingredients, multiple breath-freshening ingredients, breath-freshening ingredients and antimicrobial ingredients, multiple appetite suppressors, acids and bases that react to effervesce, a bitter compound with a high-intensity sweetener, a cooling agent and an appetite suppressant, a warming agent and an appetite suppressant, a high-intensity sweetener and an appetite suppressant, a high-intensity sweetener with an acid, a probiotic ingredient and a prebiotic ingredient, a vitamin and a mineral, a metabolic enhancement ingredient with a macronutrient, a metabolic enhancement ingredient with a micronutrient, an enzyme with a substrate, a high-intensity sweetener with a sweetness potentiator, a cooling compound with a cooling potentiator, a flavor with a flavor potentiator, a warming compound with a warming potentiator, a flavor with salt, a high-intensity sweetener with salt, an acid with salt, a cooling compound with salt, a warming compound with salt, a flavor with a surfactant, an astringent compound with an ingredient to provide a sensation of hydration, etc. In some embodiments, the multiple ingredients may be part of the same delivery system or may be part of different delivery systems. Different delivery systems may use the same or different encapsulating materials.

Typically, encapsulation of the multiple ingredients will result in a delay in the release of the predominant amount of the multiple ingredients during consumption of a compressible chewing gum that includes the encapsulated multiple ingredients (e.g. as part of a delivery system added as an ingredient to the compressible chewing gum). This may be particularly helpful in situations wherein separate encapsulation of the ingredients may cause them to release with different release profiles. For example, different high-intensity sweeteners may have different release profiles because they have different water solubilities or differences in other characteristics. Encapsulating them together may cause them to release more simultaneously.

In some embodiments, the release profile of the multiple ingredients can be managed for a chewing gum by managing various characteristics of the multiple ingredients, the delivery system containing the multiple ingredients, and/or the compressible chewing gum containing the delivery system and/or how the delivery system is made in a manner as previously discussed above.

The active ingredients mentioned above are meant as examples of active ingredients which could be applicable in a chewing gum, however, this list should not be considered as exhaustive.

Active ingredients to be applied in chewing gum according to embodiments of the invention may be applied as such or be included or bonded in different ways, such as being part of an inclusion complex e.g. as described in U.S. Pat. No. 5,866, 179, which is hereby incorporated by reference. A resin-bonding of nicotine is described in e.g. WO 2006/000232 which is also incorporated herein by reference. Further conventional methods of applying active ingredients may obviously be applied within the scope of the invention.

The following examples are given for illustrative purposes and as such are given to exemplify various elements of the present invention. Example 1 illustrates how to prepare an example of a gum base. This gum base is used as basis for further elements as described in the following examples.

Example 2, 3 and 6 illustrate preparation of nicotine-containing chewing gums conventional without flavor, conventional with flavor and compressed chewing gum, respectively. These are meant for illustrating variations in possible chewing gums to be used in multi-part kits according to the present invention.

Example 4, 5, 7 and 8 illustrate preparation of pellets with variation in how to add flavor and manufacturing process. In example 4 the pellets are made with flavor solely in the coating, whereas in example 5 flavor is inside the pellets. Examples 7 and 8 are compressed pellets.

Example 9 and 10 give examples of multi-part kits with compositional and number variations, respectively.

Example 11 illustrates the nicotine release from a piece of chewing gum containing nicotine. It is noted that nicotine release is relatively slow.

Figure 6:
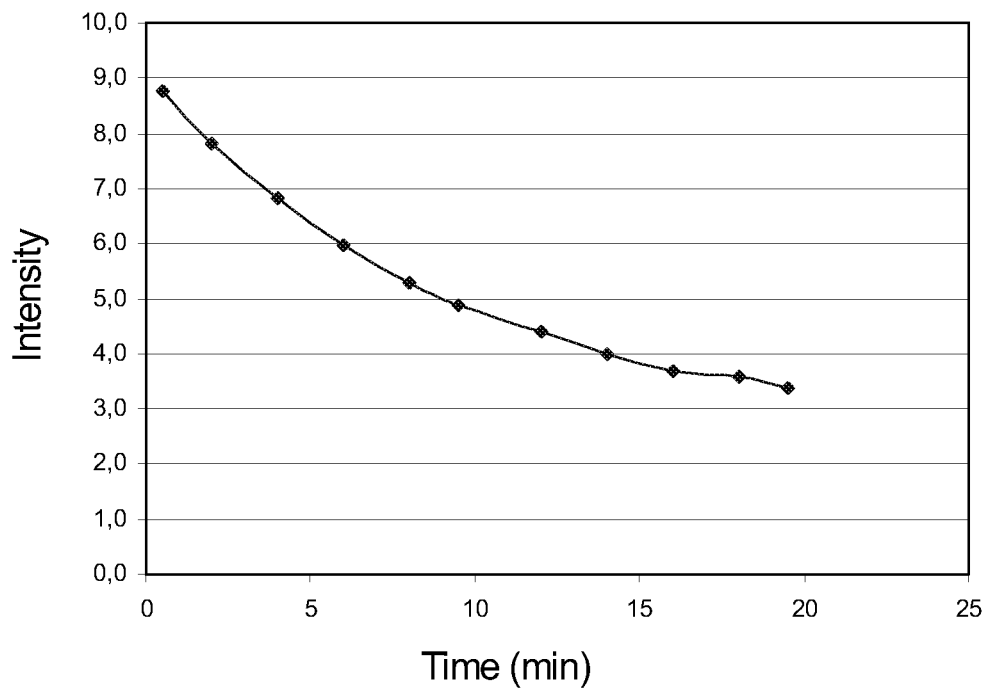
Figure 7:
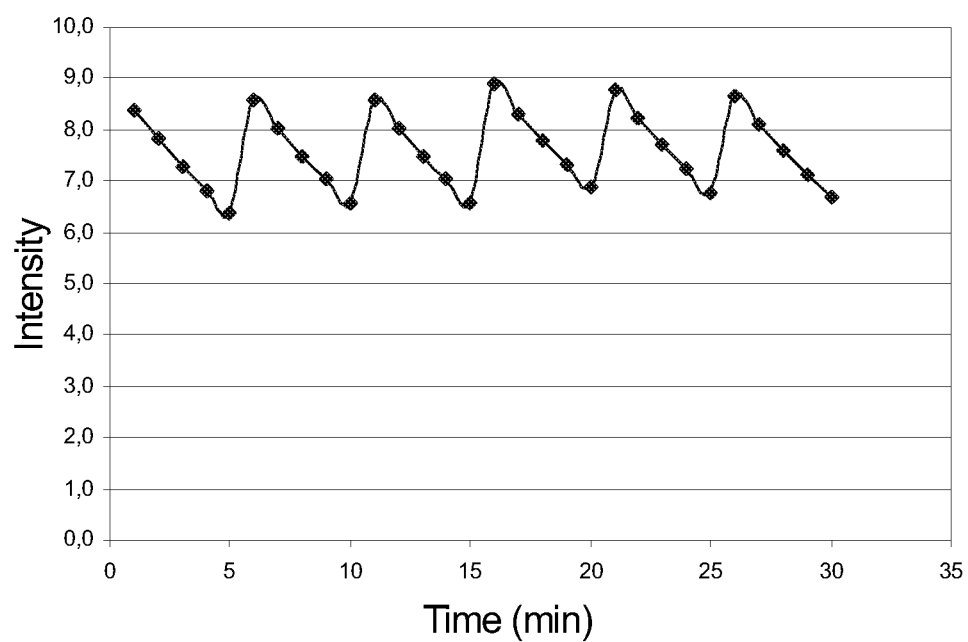

Example 12 illustrates through FIGS. 6 and 7 how flavor is effective to provide a satisfying sensory evaluation but is relatively fast released from a piece of chewing gum as compared to e.g. nicotine from example 11. The effect of supplying with flavor-containing formulations is seen.

Example 13 illustrates various combinations of gum base content of chewing gum and pellets and concludes on the importance of keeping the remainder low.

Example 14 is a stability test of chewing gum, where a conventional piece of chewing gum is supplemented with a commercially available sweet.

EXAMPLE 1

Preparation of Gum Base

A gum base is prepared, which comprises the following ingredients.

| Ingredients | Percent by weight |
| --- | --- |
| Elastomer | 10 |
| Natural resin | 28 |
| Synthetic resin | 22 |
| Fat/wax/emulsifiers | 23 |
| Fillers | 14 |
| Flavors | 3 |

It should be emphasized that several other gum base compositions may be applied within the scope of the invention.

The elastomer and filler are added to a mixing kettle provided with mixing means like e.g. horizontally placed Z-shaped arms. The kettle has been preheated for 15 minutes to a temperature of about 120° C. The rubber is broken into small pieces and softened with mechanical action in the kettle.

The resin is slowly added to the elastomer until the mixture becomes homogeneous. The remaining resin is then added to the kettle and mixed for 10-20 minutes. The softening ingredients are added and mixed for 20-40 minutes until the whole mixture becomes homogeneous.

The mixture is then discharged into the pan and allowed to cool to room temperature from the discharged temperature of 120° C.

EXAMPLE 2

Preparation of Nicotine-Containing Chewing Gum Cores without Flavor

Chewing gum cores are prepared by use of the gum base in example 1 and according to a conventional mechanical mixing procedure during moderate use of heating as described below.

| | |
| --- | --- |
| Gum base | 57.4% |
| Filler | 17.6% |
| Nicotine Polacrilex | |
| Nicotine | 0.2% |
| Ion exchange resin | 0.8% |
| Buffer agents | |
| Sodiumhydrogencarbonate | 1.0% |
| Sodium carbonate | 2.0% |
| Sorbitol powder | 19.1% |
| Liquid sweetener | 1.5% |
| Intense sweetener | 0.4% |

Gum base and filler are mixed in a mixing kettle provided with mixing means like e.g. horizontally placed Z-shaped arms. The kettle has been preheated to a temperature of up to approximately 50° C.

When the content is homogenous the other ingredients are added according to a specified time schedule. Nicotine is added in the first half of the mixing process and can be added as pure nicotine, as a nicotine salt or bound to an ion exchange resin, e.g. Amberlite IRP 64.

The chewing gum cores may be formulated with 0.1-8 mg of nicotine per piece preferably 2 or 4 mg. The API-containing chewing gum pieces of the examples herein comprise 2 mg nicotine complex unless otherwise stated.

EXAMPLE 3

Preparation of Nicotine-Containing Chewing Gum Cores Containing Flavor

Chewing gum cores are prepared by use of the gum base in example 1 and according to a conventional mechanical mixing procedure during moderate use of heating as described below.

|  |  |
|---|---|
| Gum base | 42% |
| Filler | 10% |
| Nicotine Polacrilex |  |
| Nicotine | 0.2% |
| Ion exchange resin | 0.8% |
| Buffer agents |  |
| Sodiumhydrogencarbonate | 1.0% |
| Sodium carbonate | 2.0% |
| Sorbitol powder | 41% |
| Intense sweetener | 0.5% |
| Flavor | 2.5% |

Gum base and filler are mixed in a mixing kettle provided with mixing means like e.g. horizontally placed Z-shaped arms. The kettle has been preheated to a temperature of up to approximately 50° C.

When the content is homogenous the other ingredients are added according to a specified time schedule. Nicotine is added in the first half of the mixing process and can be added as pure nicotine, as a nicotine salt or bound to an ion exchange resin, e.g. Amberlite IRP 64.

The chewing gum cores may be formulated with 0.1-8 mg of nicotine per piece preferably 2 or 4 mg. The API-containing chewing gum pieces of the examples herein comprise 2 mg nicotine complex unless otherwise stated.

EXAMPLE 4

Preparation of Pellets Containing Chewing Gum with Flavor in the Coating

Flavor pellets containing chewing gum cores are prepared by use of the gum base of example 1.

Gum base pellets are sorted to obtain round pellets in the range of 40-70 mg of gum base.

Gum base pellets were placed in a coating pan and rotated for a few minutes. Small amounts of talc were added at this stage to prevent the cores from sticking together.

The gum base pellets were provided with a hard coating with flavor in the coat; in this example the coat contained xylitol, mannitol, gum Arabic, polysorbate, sucralose and flavor; in this example 4 mg of orange flavor pr. pellet. In total 250 mg of coating were applied.

Optional coatings may e.g. be applied according to the methods disclosed in U.S. Pat. No. 6,627,234, hereby incorporated by reference.

EXAMPLE 5

Preparation of Pellets Containing Chewing Gum with Flavor

Chewing gum cores are prepared by use of the gum base in example 1 and according to a conventional mechanical mixing procedure during moderate use of heating as described below.

|  |  |
|---|---|
| Gum base | 16% |
| Bulk sweetener | 78% |
| High Intense sweetener | 2% |
| Flavor | 4% |

The gum base ingredients are mixed in a mixing kettle provided with mixing means like e.g. horizontally placed Z-shaped arms. The kettle has been preheated to a temperature of up to approximately 50° C.

When the content is homogenous the other ingredients are added according to a specified time schedule.

Gum cores are conditioned and rolled and scored into pieces of 250 mg.

The gum core is loaded into a pan and carnauba wax is added to polish the cores.

EXAMPLE 6

Compressed Chewing Gum Tablets Containing Nicotine

Gum base from example 1 is processed into granules as follows:

To form the gum base as granules, the prepared gum base is transferred either directly or in the form of pellets to an extruder (here a Leistritz ZSE/BL 360 kw 104, available from Leistritz GmbH, Germany), which extrudes the gum base through a die plate into a liquid filled chamber (here a granulator A5 PAC 6, available from GALA GmbH, Germany). Descriptions of the extruder and the granulator may be found in e.g. WO 2004/098305, incorporated herein by reference.

The already prepared gum base composition is added at a first inlet of the extruder.

The extruder delivers the gum base-comprising composition at a feed rate of 400 kg/h to the die plate. An extruder screw speed set at 247 rpm is applied, and the temperature in the extruder is in the range of 40° C. to 70° C. along about ¾ of the extruder barrel length, until the composition passes a heating device in the outlet end of the extruder. Here the composition is heated to an extruder exit temperature of about 109° C. The extruder and the granulator produce a pressure difference of about 70-75 bar.

The composition is extruded through the die plate, which is here a die plate having 696 holes with a diameter of 0.36 mm and being heated to a temperature of about 177° C. In the granulator chamber the extruded composition is cut to granules by a cutter with 8 blades and cutter speed set at 1999 rpm. The particles are cooled and transported to the strainer unit (here a centrifugal dryer TWS 20, available from GALA GmbH, Germany) in water with temperature about 11° C. and flow about 22 m³/h. The average cooling and transport time in water is approx. 60 seconds. The particle rate is 400 kg/h and the average diameter of the obtained particles is here obtained to be 0.93 mm.

The cooling and transport stage carried out in water in this example could be carried out in other media such as e.g. air as well. Also various alternative apparatuses, die plates, settings, etc. could be applied in order to obtain smaller or larger average particle sizes of the prepared granules.

Gum base granules (40% by weight of the total chewing gum tablet) were mixed with bulk sweetener (57.4%, by weight of the total chewing gum tablet), nicotine polacrilex (1.1% by weight of the total chewing gum tablet) and tabletting aid (1.5% by weight of the total chewing gum tablet).

The mixture was compressed into chewing gum tablets having a weight of approximately 1.5 g each.

EXAMPLE 7

Preparation of Compressed Pellets Containing Flavor and Chewing Gum

Gum base from example 1 is processed into granules as described in example 6.

Gum base granules (10% by weight of the total chewing gum tablet) were mixed with bulk sweetener (84.7%, by weight of the total chewing gum tablet), flavor (5% by weight of the total chewing gum tablet) and sweetener (0.3% by weight of the total chewing gum tablet).

The mixture was compressed into chewing gum tablets having a weight of approximately 250 mg each.

EXAMPLE 8

Preparation of Compressed Pellets Containing Flavor and not Chewing Gum

Bulk sweetener (94.7% by weight of the total tablet) was mixed with tutti flavor (5% by weight of the total tablet) and sweetener (0.3% by weight of the total tablet).

The mixture was compressed into chewing gum tablets having a weight of approximately 400 mg each.

EXAMPLE 9

Multi-Part Kits—Compositional Variations

Different combinations of chewing gum and pellets were combined in multi-part kits. Some of the combinations can be seen in the table below. Obviously a further large number of combinations may be carried out within the scope of the present invention.

The flavors may be combined in a large number of ways, the below combinations are merely some examples.

The number of different flavors in the pellets may be varied likewise, examples are shown here of between 1 and 8 different flavors of the pellets.

The individual pellets will typically be single-flavored; however obviously each pellet may as well comprise two or more flavors in combination.

All shown kits are with nicotine as the API; obviously the kits may be made in similar ways with other APIs.

| Kit | Chewing gum | Nicotine content | Pellets | Flavors in the pellets |
|---|---|---|---|---|
| A | Ex. 3 | 2 mg | Ex. 4 | Orange, spearmint, cinnamon, mint |
| B | Ex. 3 | 2 mg | Ex. 5 | Lemon, orange, blackcurrant, liquorice |
| C | Ex. 3 | 2 mg | Ex. 7 | Orange, spearmint, cinnamon, wintergreen |
| D | Ex. 3 | 2 mg | Ex. 8 | Strawberry, lime, menthol, apple |
| E | Ex. 3 | 4 mg | Ex. 4 | Strawberry, orange |
| F | Ex. 3 | 4 mg | Ex. 5 | Liquorice, lemon |
| G | Ex. 3 | 4 mg | Ex. 7 | Peppermint, cherry, lime |
| H | Ex. 3 | 4 mg | Ex. 8 | Pineapple, mint, spearmint, orange |
| I | Ex. 6 | 2 mg | Ex. 4 | Orange, spearmint, cinnamon, mint |
| J | Ex. 6 | 2 mg | Ex. 5 | Lemon, orange, blackcurrant, liquorice |
| K | Ex. 6 | 2 mg | Ex. 7 | Orange, spearmint, cinnamon, wintergreen |
| L | Ex. 6 | 2 mg | Ex. 8 | Strawberry, lime, menthol, apple |
| M | Ex. 6 | 4 mg | Ex. 4 | Orange |
| N | Ex. 6 | 4 mg | Ex. 5 | Liquorice, lemon |
| O | Ex. 6 | 4 mg | Ex. 7 | Peppermint, cherry, lime |
| P | Ex. 6 | 4 mg | Ex. 8 | Pineapple, mint, spearmint, orange |
| Q | Ex. 6 with mint flavor | 2 mg | Ex. 4 | Orange, spearmint, cinnamon, mint, strawberry, lemon |
| R | Ex. 6 with mint flavor | 2 mg | Ex. 5 | Lemon, orange, blackcurrant, liquorice |
| S | Ex. 6 with mint flavor | 2 mg | Ex. 7 | Orange, spearmint, cinnamon, wintergreen, menthol, blackcurrant, mint, apple |
| T | Ex. 6 with mint flavor | 2 mg | Ex. 8 | Strawberry, lime, menthol, apple |
| U | Ex. 6 with mint flavor | 4 mg | Ex. 4 | Strawberry, orange |
| V | Ex. 6 with mint flavor | 4 mg | Ex. 5 | Lemon |
| W | Ex. 6 with mint flavor | 4 mg | Ex. 7 | Peppermint, cherry, lime |
| X | Ex. 6 with mint flavor | 4 mg | Ex. 8 | Pineapple, blackcurrant, mint, spearmint, orange, cinnamon, menthol, lemon |
| Y | Ex. 6 with mint flavor | 2 mg | Ex. 8 | Mint |

EXAMPLE 10

Multi-Part Kits—Number Variation

Different combinations of numbers of chewing gum and pellets were combined in multi-part kits on the basis of kit A above. The flavor pellets were equally distributed between the four various flavors, however obviously within the scope of the invention, there may as well be combined according to the other embodiments shown in the preceding example.

| Kit | # of chewing gum | # of flavor pellets |
|---|---|---|
| AA | 1 | 9 |
| AB | 5 | 10 |
| AC | 5 | 25 |
| AD | 10 | 40 |
| AE | 10 | 60 |
| AF | 10 | 80 |
| AG | 20 | 80 |
| AH | 20 | 120 |
| AI | 20 | 160 |

EXAMPLE 11

Nicotine Release from Chewing Gum

A piece of the chewing gum of example 2 comprising 2.0 mg nicotine as the active pharmaceutical ingredient was chewed by a test person in accordance with standard instructions for using nicotine chewing gum. At certain intervals during chewing, the amount of released nicotine was measured in relation to the initial amount of nicotine in the chewing gum. The results are indicated in the table below.

| Time (min) | Nicotine released (mg) | Nicotine left in chewing gum (mg) | Relative amount of nicotine left (Wt %) |
|---|---|---|---|
| 0 | 0 | 2.0 | 100 |
| 10 | 0.8 | 1.2 | 60 |
| 30 | 1.5 | 0.5 | 25 |
| 120 | 1.9 | 0.1 | 5 |

As can be seen from the table, in order to avoid unnecessary loss of nicotine, it is highly desirable that the chewing gum is not thrown away too early in the chewing process.

Therefore, most packages of nicotine chewing gum on the market comprise instructions to keep the chewing gum in the mouth for a period of approximately 30 min.

This confirms the need for the embodiments according to the present invention, in which users are motivated to keep the chewing gum for 30 minutes or more by improved taste-experience through the addition of more flavor from flavor-containing formulations.

EXAMPLE 12

Flavor Intensity

FIG. 6 is a graphical representation of the results from a sensory test panel indicating the flavor intensity from a conventional piece of confectionery chewing gum over time. The chewing gum used was without API in order to clearly mark the flavor intensity of the chewing gum.

The scale used for indicating the flavor intensity was 0 to designate very weak and 15 to designate very strong. It was seen that the flavor intensity after app. ½ min was close to 9 and throughout the remaining part of the chewing process, the intensity was smoothly decreasing over time.

In a chewing gum comprising an API, the taste of the API may be directly unpleasant or the API may influence the taste of the other ingredients in a worse direction. Therefore a further experiment was carried out to check the result, when a flavor-containing formulation was inserted into the mouth for each 5 minutes of chewing. The result of this test is seen in FIG. 7.

By comparing FIGS. 6 and 7 can be seen that a pleasant relatively high level of taste is maintained in the chewing gum over a period of 30 minutes. For a piece of chewing gum comprising an API such as nicotine, this high level of taste may be able to make it pleasant to chew an API chewing gum in a period of 30 minutes.

In this regard it should be noted that the release profile for individual APIs tend to differ from each other, sometimes even with large difference from one to another. Hence the necessity of maintaining a high level of taste may deviate from one API to another; for instance for nicotine, the release of nicotine is somewhat slower than for most flavors used; thus it will most often be necessary to maintain a high level of taste for a nicotine chewing gum, in case a pleasant tasting chewing gum is desired.

EXAMPLE 13

Various Combinations of Gum Base Content of Chewing Gum and Pellets

The gum base content in the chewing gum and the pellets, respectively, was varied in order to investigate the remainder after chewing. What is most important relating to the sensory properties in respect of size of the remainder in the mouth is which volume is left in the mouth. This volume is primarily caused by the gum base content. Obviously a certain amount of other ingredients than the gum base will also be left over; however these will primarily fill up in between the polymers of the gum base.

Therefore in the table below, for the sake of clarity, the evaluation from the sensory panel is mainly done on the basis of the volume of the remainder and then this evaluation is linked to the accumulated gum base content.

| Kit | Gum base content in chewing gum (mg) | Gum base content in pellets (mg) | Number of pellets in 30 min | Accumulated gum base content (mg) | Evaluation |
|---|---|---|---|---|---|
| BA | 480 | 50 | 5 | 730 | Excellent |
| BB | 574 | 40 | 4 | 734 | Excellent |
| BC | 239 | 40 | 6 | 479 | Excellent |
| BD | 574 | 550 | 5 | 3324 | Unacceptable |
| BE | 200 | 100 | 3 | 500 | Excellent |
| BF | 300 | 200 | 2 | 700 | Excellent |
| BG | 50 | 10 | 3 | 80 | Unacceptable |
| BH | 574 | 0 | 6 | 574 | Excellent |
| BI | 500 | 700 | 5 | 4000 | Unacceptable |
| BJ | 480 | 15 | 20 | 780 | Excellent |

On the basis of the experiments it was concluded that, as a general rule, that certain intervals of gum base in the mouth at a time was preferred. This is summed up in the table below. However these intervals should not necessarily be taken as definite limits but as an indication of which ranges to avoid in order to increase the possibility of a positive experience for the user.

| Gum base content in mouth of user (mg) | Evaluation |
|---|---|
| Up to 200 | Unacceptable |
| 200-300 | Acceptable |
| 300-400 | Preferred |
| 400-800 | Most preferred |
| 800-1000 | Preferred |
| 1000-3000 | Acceptable |
| 3000 and above | Unacceptable |

The above kits BA-BI were evaluated over a chewing process of 30 min; obviously depending on which API is present in the chewing gum this chewing time may be longer or shorter.

In order to be able to supplement with a number of flavor-containing compositions, it is seen that the gum base content of these should preferably not be too high. In combination with the fact that the amount of gum base in the starting piece of chewing gum should not be too low as described elsewhere herein, it seems favorable to keep the amount of gum base in the flavor-containing compositions lower than the gum base content of the pieces of chewing gum.

EXAMPLE 14

Stability Test of Chewing Gum

A piece of the chewing gum of example 2 comprising 2.0 mg nicotine as the active pharmaceutical ingredient was chewed by a test person in accordance with standard instructions for using nicotine chewing gum.

At regular intervals during chewing, the test person supplemented the chewing gum with a commercially available sweet of approximately 0.5 g containing flavor and sugar in order to improve the taste. The sweet comprised a combination of sugar, fructose, rice starch, dextrin, gum arabic, flavorings, carnauba wax, and magnesium stearate.

Following 10 sweets the chewing gum comprising nicotine was observed to crumble, i.e. the gum base was dissolved by the sweets. This was observed to be highly dissatisfactory.

This dissolving is due to some of the ingredients of the sweet, it is not fully known which, but a number of ingredients used in commercially available sweets could cause such dissolving. Hence it is an important feature in relation to embodiments of the present invention that the composition of the pellets substantially does not affect the gum base.

Moreover it has been found that some ingredients which may be used in commercially available sweets may cause deactivation of some active pharmaceutical ingredients.

The flavor-containing compositions used in kits according to embodiments of the present invention can indeed be combined with chewing gum without affecting the gum base in a negative manner or risk deactivation of the active pharmaceutical ingredients used.

It should be understood that the above examples are indicative of the combinations which may be carried out according to embodiments of the present invention. I.e. in the examples wherein flavor is used a number of different other flavors may be used as well according to embodiments of the present invention.

Moreover according to embodiments of the present invention examples 4 and 5 may be combined in order to obtain pellets comprising flavor in both the core and the coat.

The compressed chewing gum of example 6 may according to embodiments of the present invention include flavor as well in a suitable amount.

What is claimed is:

1. A multi-part kit for administering at least one active pharmaceutical ingredient comprising:
   at least one piece of chewing gum comprising said active pharmaceutical ingredient, said piece of chewing gum comprising gum base;
   at least one further flavor-containing formulation;
   wherein said at least one further flavor-containing formulation forms a further piece separate and distinct from said at least one piece of chewing gum,
   wherein the gum base content of said at least one further flavor-containing formulation is less than 70% by weight of the gum base content of said at least one piece of chewing gum; and
   consumer packaging comprising at least one first compartment containing said at least one piece of chewing gum and at least one second compartment containing said at least one further flavor-containing formulation.

2. The multi-part kit according to claim 1, wherein said at least one further flavor-containing formulation is free of gum base.

3. The multi-part kit according to claim 1, wherein the gum base content of said at least one further flavor-containing formulation is less than 40% by weight of the gum base content of said at least one piece of chewing gum.

4. The multi-part kit according to claim 1, wherein the gum base content of said at least one further flavor-containing formulation is more than 4% by weight of the gum base content of said at least one piece of chewing gum.

5. The multi-part kit according to claim 1, wherein at least one of said at least one further flavor-containing formulation comprises a flavor different from any flavor in said at least one piece of chewing gum.

6. The multi-part kit according to claim 1, wherein at least one of said at least one further flavor-containing formulation comprises a flavor being the same as a flavor in said at least one piece of chewing gum.

7. The multi-part kit according to claim 1, wherein said at least one further flavor-containing formulation comprises at least two formulations with different flavors.

8. The multi-part kit according to claim 1, wherein said at least one further flavor-containing formulation is a pellet.

9. The multi-part kit according to claim 1, wherein said at least one further flavor-containing formulation comprises flavor selected from the group consisting of cinnamon, wintergreen, spearmint, orange, tutti, peppermint, menthol and lemon.

10. The multi-part kit according to claim 1, wherein said active pharmaceutical ingredient is a tobacco alkaloid.

11. The multi-part kit according to claim 1, wherein a ratio of number of flavor-containing formulations and number of pieces of chewing gum of said multi-part kit is above 2.

12. The multi-part kit according to claim 1, wherein said consumer packaging comprises individually sealed compartments.

13. The multi-part kit according to claim 1, wherein said consumer packaging comprises a plastic box or a blister-package.

14. The multi-part kit according to claim 1,
   wherein said multi-part kit comprises
   at least one piece of chewing gum comprising gum base and nicotine; and
   one or more pieces of flavor-containing pellets comprising gum base,
   wherein the gum base content of said pieces of flavor-containing pellets is less than 70% by weight of the gum base content of said piece of chewing gum.

15. An assortment of at least two multi-part kits;
   each of said at least two multi-part kits comprises at least one piece of chewing gum comprising at least one active pharmaceutical ingredient, and
   each of said at least two multi-part kits further comprises at least one further flavor-containing formulation, wherein said at least one further flavor-containing formulation forms a further piece separate and distinct from said at least one piece of chewing gum;
   said at least one piece of chewing gum comprises gum base;
   said at least one active pharmaceutical ingredient of the individual pieces of chewing gum is the same for each of the at least two multi-part kits;
   the at least one further flavor-containing formulation of a first multi-part kit comprises at least one flavor different from flavors of the at least one further flavor-containing formulation of a second multi-part kit; and
   each of said at least two multi-part kits comprises consumer packaging comprising at least one first compartment containing said at least one piece of chewing gum and at least one second compartment containing said at least one further flavor-containing formulation.

16. The assortment of at least two multi-part kits according to claim 15, wherein the gum base content of said at least one further flavor-containing formulation is less than 70% by weight of the gum base content of said piece of chewing gum.

17. An assortment of at least two multi-part kits, wherein said multi-part kits are multi-part kits according to claim 1.

18. A method of administering at least one pharmaceutically active ingredient being part of the multi-part kit of claim 1, said method comprising the steps of:
   administering at least one piece of chewing gum comprising said at least one pharmaceutically active ingredient, and
   administering at least one further flavor-containing formulation after a time interval of chewing said piece of chewing gum to maintain a satisfying taste for a longer period of time while releasing said pharmaceutically active ingredient.

19. The method of administering at least one pharmaceutically active ingredient according to claim 18, wherein the time interval between administering said at least one piece of chewing gum to administering said at least one further flavor-containing formulation is at least 15 seconds.

20. The method of administering at least one pharmaceutically active ingredient according to claim 18, wherein the time interval between administering said at least one piece of chewing gum to administering said at least one further flavor-containing formulation is at most 20 minutes.

21. The method of administering at least one pharmaceutically active ingredient according to claim 18, wherein said at least one further flavor-containing formulation is supplemented with at least one further flavor-containing formulation after at least about 3 to 9 minutes, and again after at least about 10 to 18 minutes.

22. The method of administering at least one pharmaceutically active ingredient according to claim 18, wherein said at least one further flavor-containing formulation is supplemented with at least one further flavor-containing formulation after at least about 3 to 7 minutes, again after at least about 7 to 12 minutes, again after at least about 12 to 18 minutes, and again after at least about 18 to 28 minutes.

23. The method of administering at least one pharmaceutically active ingredient according to claim 18, wherein chewing said piece of chewing gum continues for more than 5 minutes.

24. The multi-part kit according to claim 10, wherein said tobacco alkaloid is nicotine, wherein said nicotine is in a form selected from the group consisting of nicotine salts, nicotine free base, encapsulated nicotine, nicotine bound in a complex, and any combination thereof.

\* \* \* \* \*